(12) United States Patent
Rybak et al.

(10) Patent No.: US 8,088,606 B2
(45) Date of Patent: Jan. 3, 2012

(54) **METHOD FOR PRODUCING AN L-AMINO ACID USING BACTERIUM OF THE *ENTEROBACTERIACEAE* FAMILY WITH ATTENUATED EXPRESSION OF A GENE CODING FOR SMALL RNA**

(75) Inventors: Konstantin Vyacheslavovich Rybak, Moscow (RU); Aleksandra Yurievna Skorokhodova, Moscow (RU); Elvira Borisovna Voroshilova, Moscow (RU); Mikhail Markovich Gusyatiner, Moscow (RU); Tatyana Viktorovna Leonova, Moscow (RU); Vitaly Grigorievich Paraskevov, Moscow (RU); Takuji Ueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/858,658

(22) Filed: Aug. 18, 2010

(65) Prior Publication Data

US 2010/0311129 A1 Dec. 9, 2010

Related U.S. Application Data

(63) Continuation of application No. 12/212,743, filed on Sep. 18, 2008, now Pat. No. 7,803,584, which is a continuation of application No. PCT/JP2007/056752, filed on Mar. 22, 2007.

(30) Foreign Application Priority Data

| Mar. 23, 2006 | (RU) | 2006109062 |
| Mar. 23, 2006 | (RU) | 2006109063 |
| Apr. 11, 2006 | (RU) | 2006111808 |
| Apr. 11, 2006 | (RU) | 2006111809 |
| May 4, 2006 | (RU) | 2006115067 |
| May 4, 2006 | (RU) | 2006115068 |
| May 4, 2006 | (RU) | 2006115070 |
| Jun. 2, 2006 | (RU) | 2006119216 |
| Jul. 4, 2006 | (RU) | 2006123751 |
| Jan. 16, 2007 | (RU) | 2007101437 |
| Jan. 16, 2007 | (RU) | 2007101440 |

(51) Int. Cl.
*C12P 13/04* (2006.01)
*C12N 9/00* (2006.01)
*C12N 1/20* (2006.01)
*C12N 15/00* (2006.01)
*C07H 21/02* (2006.01)

(52) U.S. Cl. .......... 435/106; 435/183; 435/252.3; 435/320.1; 536/23.1

(58) Field of Classification Search .......... None
See application file for complete search history.

(56) References Cited

U.S. PATENT DOCUMENTS

| 5,175,107 A | 12/1992 | Debabov et al. |
| 5,688,671 A | 11/1997 | Sugimoto et al. |
| 5,932,453 A | 8/1999 | Kikuchi et al. |
| 6,132,999 A | 10/2000 | Debabov et al. |
| 6,228,638 B1 | 5/2001 | Romeo |
| 6,303,348 B1 | 10/2001 | Livshits et al. |
| 6,319,696 B1 | 11/2001 | Kishino et al. |
| 6,960,455 B2 | 11/2005 | Livshits et al. |
| 7,138,266 B2 | 11/2006 | Debabov et al. |
| 7,179,623 B2 | 2/2007 | Livshits et al. |
| 7,186,531 B2 | 3/2007 | Akhverdian et al. |
| 7,259,003 B2 | 8/2007 | Livshits et al. |
| 7,300,786 B2 | 11/2007 | Klyachko et al. |
| 7,306,933 B2 | 12/2007 | Van Dien et al. |
| 7,312,058 B2 | 12/2007 | Kashiwagi et al. |
| 7,399,618 B2 | 7/2008 | Klyachko et al. |
| 7,422,880 B2 | 9/2008 | Rybak et al. |
| 7,618,803 B2 | 11/2009 | Tabolina et al. |
| 7,618,804 B2 | 11/2009 | Tabolina et al. |
| 7,771,976 B2 | 8/2010 | Gulevich et al. |
| 2002/0110876 A1 | 8/2002 | Miyata et al. |
| 2004/0132165 A1 | 7/2004 | Akhverdian et al. |
| 2005/0048631 A1 | 3/2005 | Klyachko et al. |
| 2005/0191684 A1 | 9/2005 | Zimenkov et al. |
| 2005/0214911 A1 | 9/2005 | Marchenko et al. |
| 2005/0239175 A1 | 10/2005 | Tabolina et al. |
| 2005/0239177 A1 | 10/2005 | Livshits et al. |
| 2006/0014257 A1 | 1/2006 | Katashkina et al. |
| 2006/0019355 A1 | 1/2006 | Ueda et al. |
| 2006/0035346 A1 | 2/2006 | Savrasova et al. |
| 2006/0035348 A1 | 2/2006 | Gulevich et al. |
| 2006/0040365 A1 | 2/2006 | Kozlov et al. |
| 2006/0063240 A1 | 3/2006 | Katashkina et al. |
| 2006/0088919 A1 | 4/2006 | Rybak et al. |
| 2006/0141586 A1 | 6/2006 | Rybak et al. |
| 2006/0160191 A1 | 7/2006 | Kataoka et al. |
| 2006/0216796 A1 | 9/2006 | Hashiguchi et al. |
| 2007/0004014 A1 | 1/2007 | Tsuji et al. |
| 2007/0212764 A1 | 9/2007 | Ptitsyn et al. |
| 2008/0113416 A1 | 5/2008 | Filippov et al. |
| 2008/0153138 A1 | 6/2008 | Livshits et al. |
| 2008/0241888 A1 | 10/2008 | Zakataeva et al. |
| 2009/0081738 A1 | 3/2009 | Filippov et al. |
| 2009/0087886 A1 | 4/2009 | Filippov et al. |
| 2009/0087887 A1 | 4/2009 | Kataoka et al. |
| 2009/0104667 A1 | 4/2009 | Asakura et al. |
| 2009/0117623 A1 | 5/2009 | Marchenko et al. |
| 2009/0137011 A1 | 5/2009 | Filippov et al. |

(Continued)

FOREIGN PATENT DOCUMENTS

| WO | WO 03/046184 | 6/2003 |
| WO | WO 2006/123763 | 11/2006 |

OTHER PUBLICATIONS

Faubladier, M., et al., "*Escherichia coli* Cell Division Inhibitor DicF-RNA of the *dicB* Operon Evidence for its Generation in Vivo by Transcription Termination and by RNase III and RNase E-dependent Processing," J. Mol. Biol. 1990;212:461-471.

(Continued)

*Primary Examiner* — Christian Fronda
(74) *Attorney, Agent, or Firm* — Shelly Guest Cermak; Cermak Nakajima LLP

(57) ABSTRACT

The present invention provides a method for producing an L-amino acid using a bacterium of the Enterobacteriaceae family, particularly a bacterium belonging to genus *Escherichia* or *Pantoea*, which has been modified to attenuate expression of a gene coding for sRNA.

3 Claims, 2 Drawing Sheets

U.S. PATENT DOCUMENTS

| | | | |
|---|---|---|---|
| 2009/0148915 | A1 | 6/2009 | Van Dien et al. |
| 2009/0155861 | A1 | 6/2009 | Rybak et al. |
| 2009/0170169 | A1 | 7/2009 | Filippov et al. |
| 2009/0191601 | A1 | 7/2009 | Gulevich et al. |
| 2009/0197302 | A1 | 8/2009 | Filippov et al. |
| 2009/0203090 | A1 | 8/2009 | Ptitsyn et al. |
| 2009/0209011 | A1 | 8/2009 | Rybak et al. |
| 2009/0215129 | A1 | 8/2009 | Rybak et al. |
| 2009/0226919 | A1 | 9/2009 | Gulevich et al. |
| 2009/0226980 | A1 | 9/2009 | Filippov et al. |
| 2009/0269819 | A1 | 10/2009 | Filippov et al. |
| 2009/0275089 | A1 | 11/2009 | Klyachko et al. |
| 2009/0275090 | A1 | 11/2009 | Ueda et al. |
| 2009/0275091 | A1 | 11/2009 | Ueda et al. |
| 2009/0275092 | A1 | 11/2009 | Kodera et al. |
| 2009/0317876 | A1 | 12/2009 | Rybak et al. |
| 2010/0013258 | A1 | 1/2010 | Rybak et al. |
| 2010/0047878 | A1 | 2/2010 | Nagai et al. |
| 2010/0143982 | A1 | 6/2010 | Filippov et al. |
| 2010/0143983 | A1 | 6/2010 | Kiryukhin et al. |
| 2010/0190217 | A1 | 7/2010 | Doi et al. |

OTHER PUBLICATIONS

Hershberg, R., et al., "A survey of small RNA-encoding genes in *Escherichia coli*," Nuc. Acids Res. 2003;31(7):1813-1820.

Majdalani, N., et al., "Bacterial Small RNA Regulators," Critical Rev. Biochem. Mol. Biol. 2005;40:93-113.

Majdalani, N., et al., "Regulation of RpoS by a novel small RNA: the characterization of RprA," Mol. Microbiol. 2001;39(5):1382-1394.

Storz, G., et al., "An Abundance of RNA Regulators," Ann. Rev. Biochem. 2005;74:199-217.

Urban, J. H., et al., "Translational control and target recognition by *Escherichia coli* small RNAs in vivo," Nuc. Acids Res. 2007;35(3):1018-1037.

International Search Report for PCT Patent App. No. PCT/JP2007/056752 (Sep. 4, 2008).

Search Report for European Patent App. No. 08171633.4 (Feb. 24, 2009).

International Preliminary Examination Report corresponding to PCT/JP2007/056752 (Oct. 2, 2008).

Bollinger, C. J. T., et al., "Impact of the small RNA RyhB on growth, physiology and heterologous protein expression in *Escherichia coli*," FEMS Microbiol. Lett. 2007;275:221-228.

Bossi, L., et al., "A small RNA downregulates LamB maltoporin in *Salmonella*," Mol. Microbiol. 2007;65(3):799-810.

Communication Pursuant to Article 94(3) EPC for EP Patent App. No. 10151961.9 (Apr. 12, 2011).

Communication Pursuant to Article 94(3) EPC for EP Patent App. No. 10151962.7 (Apr. 12, 2011).

Andersen, J., et al., "The isolation and characterization of RNA coded by the *micF* gene in *Escherichia coli*," Nucl. Acids Res. 1987;15(5):2089-2101.

Begic, S., et al., "Regulation of *Serratia marcescens ompF* and *ompC* porin genes in response to osmotic stress, salicylate, temperature and pH," Microbiol. 2006;152:485-491.

Delihas, N., et al., "*MicF*: An Antisense RNA Gene Involved in Response of *Escherichia coli* to Global Stress Factors," J. Mol. Biol. 2001;313:1-12.

Extended European Search Report for EP Patent App. No. 11153815.3 (Jun. 24, 2011).

Park, J. H. et al., "Metabolic pathways and fermentative production of L-aspartate family amino acids," Biotechnol. J., 2010; 5:560-577.

Communication pursuant to Article 94(3) EPC for EP Patent App. No. 10151962.7 (Nov. 11, 2011).

U.S. Appl. No. 11/759,419, Ueda et al., filed Jun. 7, 2007.

U.S. Appl. No. 12/022,299, Rybak et al., filed Jan. 30, 2008.

U.S. Appl. No. 12/824,826, Kozlov et al., filed Jun. 28, 2010.

Obtained PCR product

METHOD FOR PRODUCING AN L-AMINO ACID USING BACTERIUM OF THE *ENTEROBACTERIACEAE* FAMILY WITH ATTENUATED EXPRESSION OF A GENE CODING FOR SMALL RNA

This application is a continuation under 35 U.S.C. §120 of U.S. patent application Ser. No. 12/212,743, filed on Sep. 18, 2008 now U.S. Pat. No. 7,803,584, which was a continuation under 35 U.S.C. §120 of PCT Patent Application No. PCT/JP2007/056752, filed on Mar. 22, 2007, which claimed priority under 35 U.S.C. §119(a) to Russian Patent Application No. 2006109062, filed on Mar. 23, 2006, Russian Patent Application No. 2006109063, filed on Mar. 23, 2006, Russian Patent Application No. 2006111808, filed on Apr. 11, 2006, Russian Patent Application No. 2006111809, filed on Apr. 11, 2006, Russian Patent Application No. 2006115067, filed on May 4, 2006, Russian Patent Application No. 2006115068, filed on May 4, 2006, Russian Patent Application No. 2006115070, filed on May 4, 2006, Russian Patent Application No. 2006119216, filed on Jun. 2, 2006, Russian Patent Application No. 2006123751, filed on Jul. 4, 2006, Russian Patent Application No. 2007101437, filed on Jan. 16, 2007, and Russian Patent Application No. 2007101440, filed on Jan. 16, 2007, the entireties of which are hereby incorporated by reference. The Sequence Listing filed electronically herewith is also hereby incorporated by reference in its entirety (File Name: 2010-08-18T_US-275D_Seq_List; File Size: 30 KB; Date Created: Aug. 18, 2010).

BACKGROUND OF THE INVENTION

1. Field of the Invention

The present invention relates to the microbiological industry, and specifically to a method for producing an L-amino acid using a bacterium of the Enterobacteriaceae family which has been modified to attenuate expression of a gene coding for small RNA (sRNA).

2. Brief Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765). Other techniques for enhancing production yields include increasing the activities of enzymes involved in amino acid biosynthesis and/or desensitizing the target enzymes of the feedback inhibition by the resulting L-amino acid (see, for example, WO 95/16042 or U.S. Pat. Nos. 4,346,170; 5,661,012 and 6,040,160).

Another way to enhance L-amino acid production yields is to attenuate expression of a gene or several genes which are involved in degradation of the target L-amino acid, genes which are responsible for diverting the precursors of the target L-amino acid from the L-amino acid biosynthetic pathway, genes which are involved in the redistribution of carbon, nitrogen, and phosphate fluxes, and genes coding for toxins etc.

Small, untranslated RNAs are present in many different organisms, ranging from bacteria to mammals. These RNAs carry out a variety of biological functions. Many of them can function as regulators of gene expression at the posttranscriptional level, either by acting as antisense RNAs, by binding to complementary sequences of target transcripts, or by interacting with proteins. Regulatory RNAs are involved in the control of a large variety of processes such as plasmid replication, transposition in pro- and eukaryotes, phage development, viral replication, bacterial virulence, global circuits in bacteria in response to environmental changes, or developmental control in lower eukaryotes (Argaman L. et. al., Current Biology, 11: 941-50 (2001)).

Small RNA (sRNA) molecules have gained much interest recently. Many *Escherichia coli* genes are known to code for sRNAs: c0067, c0293, c0299, c0343, c0362, c0465, c0614, c0664, c0719, csrB, dicF, dsrA, ffs, gadY, gcvB, is092, is102, is 128, isrA, micC, micF, oxyS, rnpB, rprA, rybA, rybB, rydB, ryeA, ryeB, ryeC, ryeD, ryeE, ryfA, rygB, rygC, rygD, sgrS, spf, sraA, sraB, sraD, sraE, sraG, sraH, sraI, sraJ, sraK, sraL, sroA, sroB, sroC, sroD, sroE, sroF, sroG, sroH, ssrA, ssrS, t44(tff), tp2, tpke11, tpke70 (Hershberg, R., et. al., Nucleic Acids Res., 31(7):1813-20 (2003) and Vogel, J., et al, Nucleic Acids Res., 31(22): 6435-43 (2003)). Most of these genes are still uncharacterized and their cellular roles are unknown. Traditionally, most RNA molecules were thought to function as mediators that carry the information from the gene to the translational machinery. Exceptions were the transfer RNAs and ribosomal RNAs that had long been known to have functions of their own, associated also with translation. However, it is now widely acknowledged that other types of untranslated RNA molecules (sRNA) exist that are involved in a diverse range of functions, from structural through regulatory to catalytic (Hershberg, R., et al., Nucleic Acids Res. 31(7): 1813-1820 (2003)).

The sraE and rygB genes encode small, untranslated RNAs—SraE and RygB of approximately 89 nt and 83 nt in length, respectively, which are encoded within the same inter-ORF region of the genome. Interactions between the SraE RNA and Hfq protein and between the RygB RNA and Hfq have been detected, SraE RNA and RygB RNA bound Hfq quite efficiently (>30% bound) (Wassarman, K. M. et al, Genes Dev. 1; 15(13):1637-51 (2001)). There is some sequence similarity between sraE and rygB, and they are transcribed in the same direction. SraE and rygB, which are located in the same intergenic region between aas and galR, show significant sequence similarity of 77% identity over 84 nt (Hershbserg, R., et. al., Nucleic Acids Res., 31(7):1813-20 (2003)). Despite this high sequence similarity, these two sRNAs exhibit an almost mutually exclusive expression pattern: RygB levels increase around the onset of the stationary phase and decrease thereafter (Vogel, J., et al, Nucleic Acids Res., 31(22): 6435-43 (2003)), whereas SraE is produced as stationary phase progresses (Argaman, L. et al, Current Biology, 11: 941-50 (2001)).

The sroE gene encodes a small, untranslated RNA called SroE. SroE sRNA was shown to be processed from a longer transcript, that is, the upstream gcpE gene. Its 5' end was mapped to the UAA stop codon of gcpE (third nucleotide). SroE extends into the promoter region downstream of the hisS gene. Both adjacent genes and the 110 bp IGR are conserved between *E. coli* and *Salmonella* species; the SroE sequences are predicted to fold into identical two-stem-loop structures with any sequence variation confined to the loops. The rybB gene is considered to be a genuine sRNA gene. RybB is produced as a shorter processed RNA species late in growth. The estimated half life was determined in stationary phase to be 8 min. The half life of SraE in stationary phase is 16 minutes; the half life of RygB in stationary phase is 30 minutes. SraH is one of the most stable known sRNA. The half life of SraH in stationary phase is 32 minutes (Vogel, J., et al, Nucleic Acids Res., 31(22): 6435-43 (2003)).

Expression of sraE is not affected by heat or cold shock treatment during early growth. The promoter of the sraE gene is found to be active in vitro, and the transcript length is similar to that observed in vivo. Expression of the *E. coli* K12 sraA gene was investigated in cells grown to different growth phases in either rich or minimal media supplemented with glycerol and in cells subjected to heat shock or cold shock treatment. The transcript levels of sraA were constant regardless of the conditions. SraB RNA is expressed during the stationary phase only and is at the highest levels at 8 and 10 hr after dilution of the culture. The gcvB gene is expressed in the early logarithmic phase, but its production slows with cellular growth. It was found that most of the gcvB transcripts read through the first terminator and stop at the second one, and thus result in an RNA product of 205 nucleotides. GcvB RNA is not affected by heat or cold shock treatment during early growth. Minor increases in GcvB expression were detected during the stationary phase when the cells were grown in glycerol minimal medium. SraH RNA is highly abundant during the stationary phase, but low levels can be detected in exponentially growing cells as well. Expression of sraH is not affected by heat or cold shock treatment during early growth. In vitro transcription of sraH resulted in a product of approximately 120 nucleotides, which corresponds to the predicted full-length RNA (Argaman, L. et al, Current Biology, 11: 941-50 (2001)). An interaction between RyhA (SraH) RNA and Hfq, a small, highly abundant RNA-binding protein, has been detected. High-copy expression of ryhA (sraH) causes increased expression of rpoS in minimal media (Wassarman, K. M. et al, Genes Dev. 1; 15(13):1637-51 (2001)).

The dsrA gene encodes DsrA RNA, a small (87-nt) regulatory RNA of *E. coli* that acts via RNA-RNA interactions to control translation and turnover of specific mRNAs. Two targets of DsrA regulation are RpoS, the stationary-phase and stress response sigma factor (sigmas), and H-NS, a histone-like nucleoid protein and global transcription repressor (Lease R. A., et al, Proc. Natl. Acad. Sci. USA, 95(21):12456-61 (1998)). Genes regulated globally by RpoS and H-NS include stress response proteins and virulence factors for pathogenic *E. coli*. Genes induced by DsrA have been identified by using transcription profiling via DNA arrays (Lease R. A., et al, J. Bacteriol., 186(18):6179-85 (2004)). Steady-state levels of mRNAs from many genes increased with DsrA overproduction, including multiple acid resistance genes of *E. coli*. Quantitative primer extension analysis verified the induction of individual acid resistance genes in the hdeAB, gadAX, and gadBC operons. Overproduction of DsrA from a plasmid rendered the acid-sensitive dsrA mutant extremely acid resistant, confirming that DsrA RNA plays a regulatory role in acid resistance.

Both the rate of transcription initiation of the dsrA gene and the stability of DsrA RNA are regulated by temperature, increasing at low temperature (Repoila F. and Gottesman S., J. Bacteriol., 183(13):4012-23 (2001)). The dsrA promoter is temperature-sensitive (Repoila F. and Gottesman S., J. Bacteriol., 185(22):6609-14 (2003)).

DsrA RNA acts by base-pairing to activate or repress translation, or to destabilize mRNAs. Base-pairing between this regulatory RNA and its target mRNAs requires the Sm-like Hfq protein, which most likely functions as an RNA chaperone to increase RNA unfolding or local target RNA concentration (Storz G., et al, Curr. Opin. Microbiol., 7(2):140-44 (2004)).

The rprA gene encodes a 106 nucleotide regulatory RNA called RprA. As with DsrA, RprA is predicted to form three stem-loop structures. At least two small RNAs, DsrA and RprA, participate in the positive regulation of the stationary phase sigma factor RpoS translation. Unlike DsrA, RprA does not have an extensive region of complementarity to the RpoS leader, leaving its mechanism of action unclear. It was assumed that RprA is non-essential in the positive regulation (Majdalani, N., et al., Mol. Microbiol, 39(5), 1382-94 (2001)).

The *E. coli* gcvB gene encodes a small RNA transcript that is not translated in vivo. Transcription from the gcvB promoter is activated by the GcvA protein and repressed by the GcvR protein, both of which are the transcriptional regulators of the gcvTHP operon which encodes the enzymes of the glycine cleavage system. A strain carrying a chromosomal deletion of gcvB exhibits normal regulation of gcvTHP expression and glycine cleavage enzyme activity. However, this mutant has high constitutive synthesis of OppA and DppA, which are periplasmic-binding protein components of two major peptide transport systems which are normally repressed in cells growing in rich medium. The altered regulation of oppA and dppA was also demonstrated using oppA-phoA and dppA-lacZ gene fusions. Although the mechanism(s) involved in the repression by gcvB of these two genes is not known, oppA regulation appears to be at the translational level, whereas dppA regulation occurs at the mRNA level. The sequence of gcvB was shown to contain two sites for transcription termination (M. L. Urbanowski et al, Mol. Microbiol., 37: 856-68 (2000)).

The micC gene (IS063) encodes a ~100-nucleotide small-RNA transcript. The expression of this small RNA is increased at a low temperature and in minimal medium. Twenty-two nucleotides at the 5' end of this transcript have the potential to form base pairs with the leader sequence of the mRNA encoding the outer membrane protein OmpC. MicC was shown to inhibit ribosome binding to the ompC mRNA leader in vitro and to require the Hfq RNA chaperone to function (Chen, S., et al., J. Bacteriol., 186(20):6679-80 (2004)).

The ryeE gene encodes a small, untranslated RNA-RyeE RNA 86 nt in length. All known sRNA are encoded within intergenic (Ig) regions (defined as regions between ORFs). The Ig region corresponding to ryeE is highly conserved when compared to the closely related *Salmonella* and *Klebsiella pneumonia* species. An interaction between RyeE RNA and Hfq protein has been detected, RyeE RNA bounds Hfq quite efficiently (>30% bound). Overproduction of RyeE causes decreased expression of rpoS during the stationary phase in LB (Wassarman, K. M., Genes Dev., 15(13): 1637-51 (2001)).

But currently, there have been no reports of inactivating a gene coding for sRNA for the purpose of producing L-amino acids.

SUMMARY OF THE INVENTION

Aspects of the present invention include enhancing the productivity of L-amino acid-producing strains and providing a method for producing an L-amino acid using these strains.

Attenuating expression of a gene coding for sRNA can enhance production of L-amino acids, such as L-threonine, L-lysine, L-cysteine, L-methionine, L-leucine, L-isoleucine, L-valine, L-histidine, L-serine, L-alanine, L-asparagine, L-aspartic acid, L-glutamine, L-glutamic acid, L-proline, L-arginine, L-phenylalanine, L-tyrosine, and L-tryptophan.

The present invention provides a bacterium of the Enterobacteriaceae family having an increased ability to produce amino acids, such as L-threonine, L-lysine, L-cysteine, L-methionine, L-leucine, L-isoleucine, L-valine, L-histidine, L-serine, L-alanine, L-asparagine, L-aspartic acid, L-glutamine, L-glutamic acid, L-proline, L-arginine, L-phenylalanine, L-tyrosine, and L-tryptophan.

It is an aspect of the present invention to provide an L-amino acid-producing bacterium of the Enterobacteriaceae family, wherein the bacterium has been modified to attenuate expression of a gene coding for sRNA.

It is a further aspect of the present invention to provide the bacterium as described above, wherein said gene coding for sRNA is selected from the group consisting of c0067, c0293, c0299, c0343, c0362, c0465, c0614, c0664, c0719, csrB, dicF, dsrA, ffs, gadY, gcvB, is092, is102, is128, isrA, micC, micF, oxyS, rnpB, rprA, rybA, rybB, rydB, ryeA, ryeB, ryeC, ryeD, ryeE, ryfA, rygB, rygC, rygD, sgrS, spf, sraA, sraB, sraD, sraE, sraG, sraH, sraI, sraJ, sraK, sraL, sroA, sroB, sroC, sroD, sroE, sroF, sroG, sroH, ssrA, ssrS, t44(tff), tp2, tpke11, and tpke70.

It is a further aspect of the present invention to provide the bacterium as described above, wherein said expression of a gene coding for sRNA is attenuated by inactivating the gene coding for sRNA.

It is a further aspect of the present invention to provide the bacterium as described above, wherein the bacterium belongs to the genus *Escherichia*.

It is a further aspect of the present invention to provide the bacterium as described above, wherein the bacterium belongs to the genus *Pantoea*.

It is a further aspect of the present invention to provide the bacterium as described above, wherein said L-amino acid is selected from the group consisting of an aromatic L-amino acid and a non-aromatic L-amino acid.

It is a further aspect of the present invention to provide the bacterium as described above, wherein said aromatic L-amino acid is selected from the group consisting of L-phenylalanine, L-tyrosine, and L-tryptophan.

It is a further aspect of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, L-serine, L-alanine, L-asparagine, L-aspartic acid, L-glutamine, L-glutamic acid, L-proline, and L-arginine.

It is a further aspect of the present invention to provide a method for producing an L-amino acid comprising:
cultivating the bacterium as described above in a medium, and
collecting said L-amino acid from the medium.

It is a further aspect of the present invention to provide the method as described above, wherein said L-amino acid is selected from the group consisting of an aromatic L-amino acid and a non-aromatic L-amino acid.

It is a further aspect of the present invention to provide the method as described above, wherein said aromatic L-amino acid is selected from the group consisting of L-phenylalanine, L-tyrosine, and L-tryptophan.

It is a further aspect of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, L-serine, L-alanine, L-asparagine, L-aspartic acid, L-glutamine, L-glutamic acid, L-proline, and L-arginine.

The present invention is described in detail below.

DETAILED DESCRIPTION OF THE PREFERRED EMBODIMENTS

1. Bacterium of the Present Invention

Figure 1:
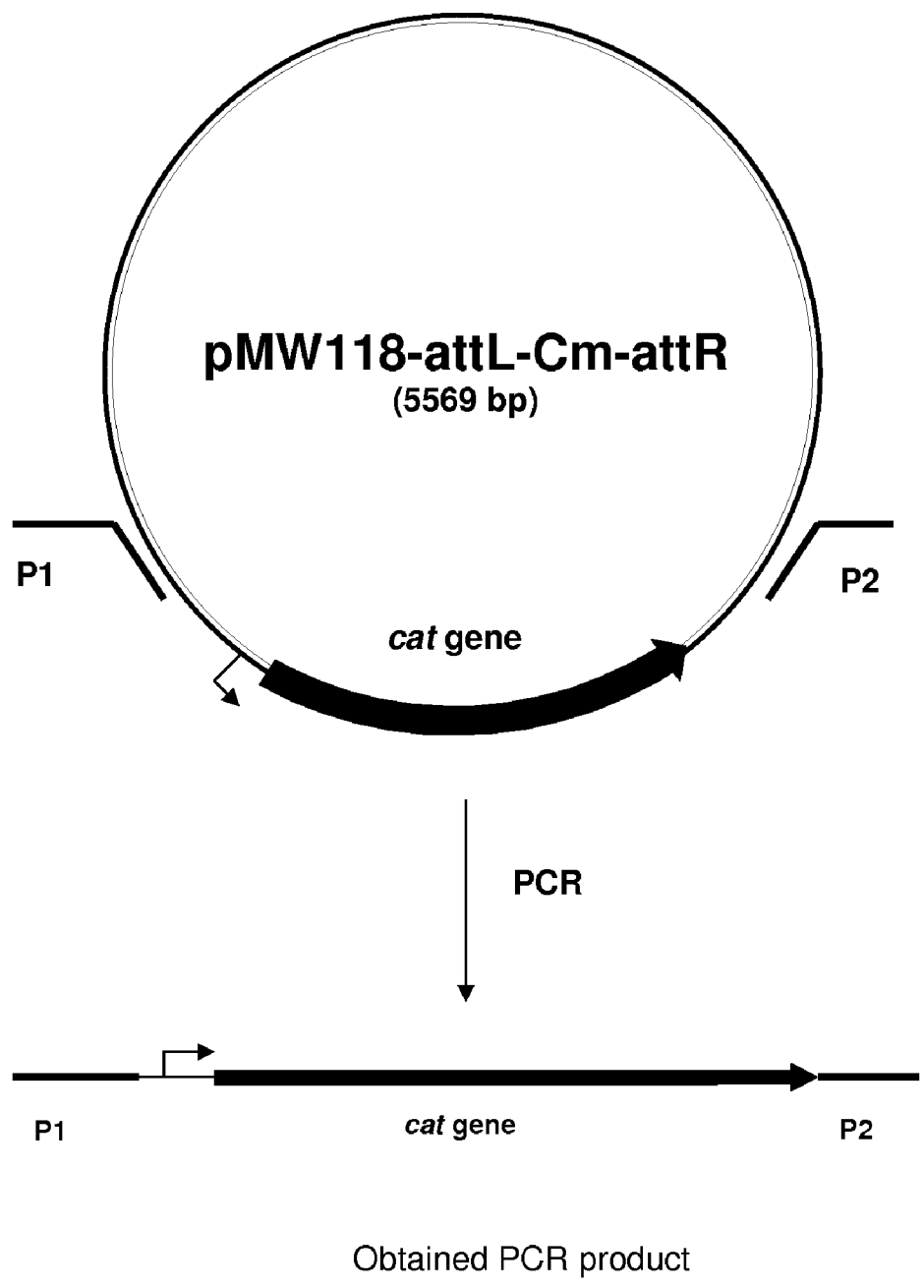
FIG. 1 shows the relative positions of primers P1 (upstream primer) and P2 (downstream primer) on plasmid pMW118-attL-Cm-attR which is used as a template for PCR amplification of the cat gene.

The bacterium of the present invention is an L-amino acid-producing bacterium of the Enterobacteriaceae family, wherein the bacterium has been modified to attenuate expression of the a gene coding for sRNA (small RNA).

The phrase "L-amino acid-producing bacterium" means a bacterium which has an ability to produce and excrete an L-amino acid into a medium, when the bacterium is cultured in the medium.

The term "L-amino acid-producing bacterium" also means a bacterium which is able to produce and cause accumulation of an L-amino acid in a culture medium in an amount larger than a wild-type or parental strain of *E. coli*, such as *E. coli* K-12, and preferably means that the microorganism is able to cause accumulation in a medium of the target L-amino acid in an amount not less than 0.5 g/L, more preferably not less than 1.0 g/L. The term "L-amino acid" includes L-alanine, L-arginine, L-asparagine, L-aspartic acid, L-cysteine, L-glutamic acid, L-glutamine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" includes L-phenylalanine, L-tyrosine, and L-tryptophan. The term "non-aromatic L-amino acid" includes L-threonine, L-lysine, L-cysteine, L-methionine, L-leucine, L-isoleucine, L-valine, L-histidine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-phenylalanine, L-tryptophan, L-proline, and L-arginine are particularly preferred.

The Enterobacteriaceae family includes bacteria belonging to the genera *Escherichia*, *Enterobacter*, *Erwinia*, *Klebsiella*, *Pantoea*, *Photorhabdus*, *Providencia*, *Salmonella*, *Serratia*, *Shigella*, *Morganella*, *Yersinia*, etc. Specifically, those classified into the Enterobacteriaceae according to the taxonomy used by the NCBI (National Center for Biotechnology Information) database (http://www.ncbi.nlm.nih.gov/htbinpost/Taxonomy/wgetorg?mode=Tree&id=1236&1v1=3&keep=1&srchmode=1&unlock) can be used. A bacterium belonging to the genus *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* as used in the present invention include, but are not limited to, *Escherichia coli* (*E. coli*).

The bacterium belonging to the genus *Escherichia* is not particularly limited, however for example, bacteria described by Neidhardt, F. C. et al. (*Escherichia coli* and *Salmonella typhimurium*, American Society for Microbiology, Washington D.C., 1208, Table 1) are encompassed by the present invention.

The phrase "a bacterium belonging to the genus *Pantoea*" means that the bacterium is classified as the genus *Pantoea* according to the classification known to a person skilled in the art of microbiology. Some species of *Enterobacter agglomerans* have been recently re-classified into *Pantoea agglom-*

*erans, Pantoea ananatis, Pantoea stewartii* or the like, based on the nucleotide sequence analysis of 16S rRNA, etc. (Int. J. Syst. Bacteriol., 43, 162-173 (1993)).

The phrase "a gene coding for sRNA" means a gene encoding an RNA that is not translated into a protein and has a small size, preferably 50 to 500 bases in length.

The phrase "bacterium has been modified to attenuate expression of a gene coding for sRNA" means that the bacterium has been modified in such a way that the modified bacterium contains a reduced amount of the sRNA, as compared with an unmodified bacterium, or is unable to synthesize the sRNA.

The phrase "inactivation of a gene coding for sRNA" means that the modified DNA region is unable to naturally express the gene due to the deletion of a part of the gene or of the gene entirely, or the modification of an adjacent region of the gene, including sequences controlling gene expression, such as promoters, enhancers, attenuators, etc.

The level of gene expression can be determined by measuring the amount of sRNA transcribed from the gene using various known methods including Northern blotting, quantitative RT-PCR, and the like.

The c0067 gene encodes the C0067 RNA. The c0067 gene (nucleotides in positions 238,462 to 238,586; GenBank accession no. NC_000913.2; gi: 49175990) is located between the yafT ORF and the yafU ORF on the chromosome of *E. coli* K-12. The nucleotide sequence of the c0067 gene is shown in SEQ ID NO: 69.

The c0293 gene encodes the C0293 RNA. The c0293 gene (nucleotides in positions 1,195,937 to 1,196,009; GenBank accession no. NC_000913.2; gi: 49175990) is located between the icd gene and the ymfD ORF on the chromosome of *E. coli* K-12. The nucleotide sequence of the c0293 gene is shown in SEQ ID NO: 70.

The c0299 gene encodes the C0299 RNA. The c0299 gene (nucleotides in positions 1,229,852 to 1,229,930; GenBank accession no. NC_000913.2; gi: 49175990) is located between the hlyE gene and the umuD gene on the chromosome of *E. coli* K-12. The nucleotide sequence of the c0299 gene is shown in SEQ ID NO:71.

The c0343 gene encodes the C0343 RNA. The c0343 gene (nucleotides in positions 1,407,387 to 1,407,461; GenBank accession no. NC_000913.2; gi: 49175990) is located between the ydaN ORF and the dbpA gene on the chromosome of *E. coli* K-12. The nucleotide sequence of the c0343 gene is shown in SEQ ID NO:72.

The c0362 gene encodes the C0362 RNA. The c0362 gene (nucleotides in positions 1,550,025 to 1,550,410; GenBank accession no. NC_000913.2; gi: 49175990) is located between the fdnI gene and the yddM ORF on the chromosome of *E. coli* K-12. The nucleotide sequence of the c0362 gene is shown in SEQ ID NO: 1.

The c0465 gene encodes the C0465 RNA. The c0465 gene (nucleotides in positions 1,970,763 to 1,970,840; GenBank accession no. NC_000913.2; gi: 49175990) is located between the tar gene and the cheW gene on the chromosome of *E. coli* K-12. The nucleotide sequence of the c0465 gene is shown in SEQ ID NO: 2.

The c0614 gene encodes the C0614 RNA. The c0614 gene (nucleotides complemented to nucleotides in positions 2,651,474 to 2,651,560; GenBank accession no. NC_000913.2; gi: 49175990) is located between the sseA gene and the IS128 gene, overlapping with the IS128 gene, on the chromosome of *E. coli* K-12. The nucleotide sequence of the c0614 gene is shown in SEQ ID NO:73.

The c0664 gene encodes the C0664 RNA. The c0664 gene (nucleotides in positions 2,833,077 to 2,833,189; GenBank accession no. NC_000913.2; gi: 49175990) is located between the ygbD gene and the hypF gene on the chromosome of *E. coli* K-12. The nucleotide sequence of the c0664 gene is shown in SEQ ID NO: 74.

The c0719 gene encodes the C0719 RNA. The c0719 gene (nucleotides in positions 3,119,380 to 3,119,601; GenBank accession no. NC_000913.2; gi: 49175990) is located between the glcA gene and the glcB gene on the chromosome of *E. coli* K-12. The nucleotide sequence of the c0719 gene is shown in SEQ ID NO: 75.

The csrB gene (synonyms—ECK2787, b4408) encodes the CsrB RNA. The csrB gene (nucleotides complementary to nucleotides in positions 2,922,178 to 2,922,537; GenBank accession no. NC_000913.2; gi: 49175990) is located between the yqcC ORF and the syd gene on the chromosome of *E. coli* K-12. The nucleotide sequence of the csrB gene is shown in SEQ ID NO: 76.

The dicF gene (synonyms—ECK1568, b1574) encodes the DicF RNA. The dicF gene (nucleotides in positions 1,647,406 to 1,647,458; GenBank accession no. NC_000913.2; gi: 49175990) is located between the rzpQ gene and the dicB gene on the chromosome of *E. coli* K-12. The nucleotide sequence of the dicF gene is shown in SEQ ID NO: 77.

The dsrA gene (synonym—b1954) encodes DsrA RNA, a global regulator of gene expression. The dsrA gene (nucleotides in positions 2,023,336 to 2,023,250; GenBank accession no. NC_000913.2; gi:49175990) is located between the yodD and yedP genes on the *E. coli* strain K-12 chromosome. The nucleotide sequence of the dsrA gene is shown in SEQ ID NO: 3.

The ffs gene (synonyms—ECK0449, b0455) encodes the Ffs RNA. The ffs gene (nucleotides in positions 475,672 to 475,785; GenBank accession no. NC_000913.2; gi: 49175990) is located between the ybaZ ORF and the ybaA ORF on the chromosome of *E. coli* K-12. The nucleotide sequence of the ffs gene is shown in SEQ ID NO: 78.

The gadY gene (synonyms—ECK3500, b4452, IS183) encodes the GadY RNA. The gadY gene (nucleotides in positions 1,647,406 to 1,647,458; GenBank accession no. NC_000913.2; gi: 49175990) is located between the rzpQ gene and the dicB gene on the chromosome of *E. coli* K-12. The nucleotide sequence of the gadY gene is shown in SEQ ID NO: 79.

The gcvB gene (synonyms: ECK2804, psrA11, IS145, b4443) encodes the GcvB RNA. The gcvB gene (nucleotides in positions 2,940,718 to 2,940,922; GenBank accession no. NC_000913.2; gi: 16130715) is located between the gcvA gene and the ygdI ORF on the chromosome of *E. coli* K-12. The nucleotide sequence of the gcvB gene is shown in SEQ ID NO: 4.

The IS092 gene (synonyms—ECK1902, b4434) encodes the IS092 RNA. The IS092 gene (nucleotides complementary to nucleotides in positions 1,985,863 to 1,986,022; GenBank accession no. NC_000913.2; gi: 49175990) is located between the yecJ ORF and the yecR ORF on the chromosome of *E. coli* K-12. The nucleotide sequence of the IS092 gene is shown in SEQ ID NO: 80.

The IS102 gene (synonyms—ECK1992, b4435) encodes the IS102 RNA. The IS102 gene (nucleotides in positions 2,069,339 to 2,069,542; GenBank accession no. NC_000913.2; gi: 49175990) is located between the yeeP ORF and the flu gene on the chromosome of *E. coli* K-12. The nucleotide sequence of the IS102 gene is shown in SEQ ID NO: 81.

The IS128 gene encodes the IS128 RNA. The IS128 gene (nucleotides in positions 2,651,537 to 2,651,745; GenBank accession no. NC_000913.2; gi: 49175990) is located between the c0614 gene and the ryfA gene, overlapping with the c0614 gene, on the chromosome of E. coli K-12. The nucleotide sequence of the IS128 gene is shown in SEQ ID NO: 82.

The isrA gene (synonyms—ECK1336, b4426, IS061) encodes the IsrA RNA. The isrA gene (nucleotides complemented to nucleotides in positions 1,403,676 to 1,403,833; GenBank accession no. NC_000913.2; gi: 49175990) is located between the abgR gene and the ydaL ORF on the chromosome of E. coli K-12. The nucleotide sequence of the isrAgene is shown in SEQ ID NO: 83.

The micC gene (synonyms: ECK1373, IS063, tke8, b4427) encodes the MicC RNA. The micC gene (nucleotides in positions 1,435,145 to 1,435,253; GenBank accession no. NC_000913.2; gi: 16127999) is located between the gene ompN and the ORF ydbK on the chromosome of E. coli K-12. The nucleotide sequence of the micC gene is shown in SEQ ID NO: 5.

The micF gene (synonyms: ECK2208, stc, b4439) encodes the MicF RNA. The micF gene (nucleotides in positions 2,311,106 to 2,311,198; GenBank accession no. NC_000913.2; gi: 16127999) is located between the ompC gene and the rcsD gene on the chromosome of E. coli K-12. The nucleotide sequence of the micF gene is shown in SEQ ID NO: 84.

The oxyS gene (synonyms—ECK3952, b4458) encodes the OxyS RNA. The oxyS gene (nucleotides complementary to nucleotides in positions 4,156,308 to 4,156,417; GenBank accession no. NC_000913.2; gi: 49175990) is located between the argH gene and the oxyR gene on the chromosome of E. coli K-12. The nucleotide sequence of the oxyS gene is shown in SEQ ID NO: 85.

The rnpB gene (synonyms—ECK3111, b3123) encodes the RnpB RNA. The rnpB gene (nucleotides complementary to nucleotides in positions 3,268,238 to 3,268,614; GenBank accession no. NC_000913.2; gi: 49175990) is located between the yhaC ORF and the garK gene on the chromosome of E. coli K-12. The nucleotide sequence of the rnpB gene is shown in SEQ ID NO: 86.

The rprA gene (synonyms—ECK1686, psrA5, IS083, b4431) encodes the RprA RNA The rprA gene of E. coli (nucleotides in positions 1,768,395 to 1,768,499; GenBank accession no. NC_000913.2; gi:49175990) is located between the ydiK ORF and the ydiL ORF on the chromosome of E. coli K-12. The nucleotide sequence of the rprA gene is shown in SEQ ID NO:6.

The rybA gene (synonyms: ECK0806, b4416) encodes the RybA RNA. The rybA gene (nucleotides complementary to nucleotides in positions 852,175 to 852,263; GenBank accession no. NC_000913.2; gi:16127999) is located between the yliL ORF and the mntR gene on the chromosome of E. coli K-12. The nucleotide sequence of the rybA gene is shown in SEQ ID NO: 87.

The rybB gene (synonyms: p25, b4417) encodes the RybB RNA. The rybB gene (nucleotides in positions 887,198 to 887,276; GenBank accession no. NC_000913.2; gi:16127999) is located between the ORF ybjK and the ORF ybjL on the chromosome of E. coli K-12. The nucleotide sequence of the rybB gene is shown in SEQ ID NO: 7.

The rydB gene (synonyms: ECK1681, tpe7, IS082, b4430) encodes the RydB RNA. The rydB gene (nucleotides complemented to nucleotides in positions 1,762,737 to 1,762,804; GenBank accession no. NC_000913.2; gi:16127999) is located between the sufA gene and the ydiH ORF on the chromosome of E. coli K-12. The nucleotide sequence of the rydB gene is shown in SEQ ID NO: 88.

The ryeA gene (synonyms: ECK1838, sraC, sraCryeA, psrA8, tkpe79, IS091, b4432) encodes the RyeA RNA. The ryeA gene (nucleotides in positions 1,921,090 to 1,921,338; GenBank accession no. NC_000913.2; gi:16127999) is located between the pphA gene and the yebY ORF, interlapping the ryeB gene which is oriented in the opposite orientation, on the chromosome of E. coli K-12. The nucleotide sequence of the ryeA gene is shown in SEQ ID NO: 89.

The ryeB gene (synonyms: ECK1839, tkpe79, IS091, b4433) encodes the RyeB RNA. The ryeB gene (nucleotides complementary to nucleotides in positions 1,921,188 to 1,921,308; GenBank accession no. NC_000913.2; gi:16127999) is located in the region of the ryeA gene on the chromosome of E. coli K-12. The nucleotide sequence of the ryeB gene is shown in SEQ ID NO: 90.

The ryeC gene (synonyms: ECK2068, QUAD1a, tp11, b4436) encodes the RyeC RNA. The ryeC gene (nucleotides in positions 2,151,299 to 2,151,447; GenBank accession no. NC_000913.2; gi:16127999) is located between the yegL ORF and the ryeD gene on the chromosome of E. coli K-12. The nucleotide sequence of the ryeC gene is shown in SEQ ID NO: 91.

The ryeD gene (synonyms: ECK2069, QUAD1b, tpe60, b4437) encodes the RyeD RNA. The ryeD gene (nucleotides in positions 2,151,634 to 2,151,776; GenBank accession no. NC_000913.2; gi:16127999) is located between the ryeC gene and the mdtA gene on the chromosome of E. coli K-12. The nucleotide sequence of the ryeDgene is shown in SEQ ID NO: 92.

The ryeE gene (synonyms: ECK2078, b4438) encodes the RyeE RNA. The ryeE gene (nucleotides in positions 2,165,136 to 2,165,221; GenBank accession no. NC_000913.2; gi: 49175990) is located between the yegQ ORF and the ogrK gene on the chromosome of E. coli K-12. The nucleotide sequence of the ryeE gene is shown in SEQ ID NO: 8.

The ryfA gene (synonyms: ECK2518, b4440) encodes the RyeE RNA. The ryeE gene (nucleotides in positions 2,651,877-2,652,180; GenBank accession no. NC_000913.2; gi: 49175990) is located between the yegQ ORF and the ogrK gene on the chromosome of E. coli K-12. The nucleotide sequence of the ryfA gene is shown in SEQ ID NO: 93.

The rygB gene (synonyms: ECK2834, PAIR2, t59, b4445, omrB) encodes the RygB RNA. The rygB gene (nucleotides complemented to nucleotides in positions 2,974,332 to 2,974,407; GenBank accession no. NC_000913.2; gi: 49175990) is located between the sraE gene and the galR gene on the chromosome of E. coli K-12. The nucleotide sequence of the rygB gene is shown in SEQ ID NO: 9. The rygB gene may be attenuated together with the adjacent sraE gene.

The rygC gene (synonyms: ECK2908, QUAD1c, t27, b4446) encodes the RygC RNA. The rygC gene (nucleotides in positions 3,054,837 to 3,054,987; GenBank accession no. NC_000913.2; gi: 49175990) is located between the sraE gene and the galR gene on the chromosome of E. coli K-12. The nucleotide sequence of the rygC gene is shown in SEQ ID NO: 94.

The rygD gene (synonyms: ECK3041, tp8, C0730, IS156, QUAD1d, b4447) encodes the RygD RNA. The rygD gene (nucleotides complementary to nucleotides in positions 3,192,773 to 3,192,992; GenBank accession no. NC_000913.2; gi: 49175990) is located between the sraE gene and the galR gene on the chromosome of E. coli K-12. The nucleotide sequence of the rygD gene is shown in SEQ ID NO: 95.

The sgrS gene (synonyms: ECK0071, ryaA, b4577) encodes the SgrS RNA. The sgrS gene (nucleotides in positions 77,367 to 77,593; GenBank accession no.

NC_000913.2; gi: 49175990) is located between the sgrR gene and the setA gene on the chromosome of *E. coli* K-12. The nucleotide sequence of the sgrS gene is shown in SEQ ID NO: 96.

The spf gene (synonyms: ECK3856, b3864, spot42) encodes the Spf RNA. The spf gene (nucleotides in positions 4,047,922 to 4,048,030; GenBank accession no. NC_000913.2; gi: 49175990) is located between the polA gene and the yihA ORF on the chromosome of *E. coli* K-12. The nucleotide sequence of the spf gene is shown in SEQ ID NO: 97.

The sraA gene (synonyms: psrA3, t15) encodes the SraA RNA. The sraA gene (nucleotides complementary to nucleotides in positions 457,952 to 458,008; GenBank accession no. NC_000913.2; gi: 49175990) is located between the clpX gene and the lon gene on the chromosome of *E. coli* K-12. The nucleotide sequence of the sraA gene is shown in SEQ ID NO:10.

The sraB gene (synonyms: psrA4, pke20) encodes the SraB RNA. The sraB gene (nucleotides in positions 1,145,811 to 1,145,979; GenBank accession no. NC_000913.2; gi:49175990) is located on the chromosome of *E. coli* K-12 upstream, but overlapping with the yceD ORF, which is oriented in the opposite direction and located upstream of sraB. The nucleotide sequence of the sraB gene is shown in SEQ ID NO: 11.

The sraD gene (synonyms: micA, ECK2682, psrA10, b4442) encodes the SraD RNA. The sraD gene (nucleotides in positions 2,812,823 to 2,812,897; GenBank accession no. NC_000913.2; gi: 49175990) is located between the luxS gene and the gshA gene on the chromosome of *E. coli* K-12. The nucleotide sequence of the sraD gene is shown in SEQ ID NO: 98.

The sraE gene (synonyms: ECK2833, psrA12, rygA, PAIR2, t59, b4444, omrA) encodes the SraE RNA. The sraE gene (nucleotides complemented to nucleotides in positions 2,974,124 to 2,974,211; GenBank accession no. NC_000913.2; gi: 49175990) is located between the aas gene and the rygB gene on the chromosome of *E. coli* K-12. The nucleotide sequence of the rygB gene is shown in SEQ ID NO: 12. The sraE gene may be attenuated together with the adjacent rygB gene.

The sraG gene (synonyms: ECK3153, psrA15, p3, b4449) encodes the SraG RNA. The sraG gene (nucleotides in positions 3,309,247 to 3,309,420; GenBank accession no. NC_000913.2; gi: 49175990) is located between the pnp gene and the rpsO gene, overlapping with the pnp gene, on the chromosome of *E. coli* K-12. The nucleotide sequence of the sraG gene is shown in SEQ ID NO: 99.

The sraH gene (synonyms: ECK3199, psrA16, ryhA, b4450) encodes the SraH RNA. The sraH gene (nucleotides in positions 3,348,599 to 3,348,706; GenBank accession no. NC_000913.2; gi: 49175990) is located between the elbB gene and the arcB gene on the chromosome of *E. coli* K-12. The nucleotide sequence of the sraH gene is shown in SEQ ID NO: 13.

The sraI gene (synonyms: ECK3426, psrA18, IS176, b4451, ryhB) encodes the SraI RNA. The sraI gene (nucleotides complemented to nucleotides in positions 3,578,946 to 3,579,039; GenBank accession no. NC_000913.2; gi: 49175990) is located between the yhhX ORF and the yhhY ORF on the chromosome of *E. coli* K-12. The nucleotide sequence of the sraI gene is shown in SEQ ID NO: 100.

The sraJ gene (synonyms: ECK3795, psrA20, ryiA, k19, b4456) encodes the SraJ RNA. The sraJ gene (nucleotides in positions 3,984,455 to 3,984,626; GenBank accession no. NC_000913.2; gi: 49175990) is located between the aslA gene and the hemY gene on the chromosome of *E. coli* K-12. The nucleotide sequence of the sraJ gene is shown in SEQ ID NO: 101.

The sraK gene (synonyms: ECK3858, psrA21, ryiB, tpk2, IS198, b4457, csrC) encodes the SraK RNA. The sraK gene (nucleotides in positions 4,049,059 to 4,049,303; GenBank accession no. NC_000913.2; gi: 49175990) is located between the yihA ORF and the yihi ORF on the chromosome of *E. coli* K-12. The nucleotide sequence of the sraK gene is shown in SEQ ID NO: 102.

The sraL gene (synonyms: ECK4056, psrA24, ryjA, b4459) encodes the SraL RNA. The sraL gene (nucleotides complemented to nucleotides in positions 4,275,950 to 4,276,089; GenBank accession no. NC_000913.2; gi: 49175990) is located between the soxR gene and the yjcD ORF, overlapping with the soxR gene, on the chromosome of *E. coli* K-12. The nucleotide sequence of the sraL gene is shown in SEQ ID NO: 103.

The sroA gene (synonym tpe79) encodes the SroA RNA. The sroA gene (nucleotides complementary to nucleotides in positions 75,516 to 75,608; GenBank accession no. NC_000913.2; gi: 49175990) is located between the tbpA gene and the sgrR gene on the chromosome of *E. coli* K-12. The nucleotide sequence of the sroA gene is shown in SEQ ID NO: 104.

The sroB gene encodes the SroB RNA. The sroB gene (nucleotides in positions 506,428 to 506,511; GenBank accession no. NC_000913.2; gi: 49175990) is located between the ybaK ORF and the ybaP ORF, overlapping with the ybaP ORF, on the chromosome of *E. coli* K-12. The nucleotide sequence of the sroB gene is shown in SEQ ID NO: 105.

The sroC gene (synonym HB_314) encodes the SroC RNA. The sroC gene (nucleotides complemented to nucleotides in positions 685,904 to 686,066; GenBank accession no. NC_000913.2; gi: 49175990) is located between the gltJ gene and the gltI gene, overlapping with the gltI gene, on the chromosome of *E. coli* K-12. The nucleotide sequence of the sroC gene is shown in SEQ ID NO: 106.

The sroD gene (synonym p24) encodes the SroD RNA. The sroD gene (nucleotides complemented to nucleotides in positions 1,886,041 to 1,886,126; GenBank accession no. NC_000913.2; gi: 49175990) is located between the rnd gene and the fadD gene, overlapping with the fadD gene, on the chromosome of *E. coli* K-12. The nucleotide sequence of the sroD gene is shown in SEQ ID NO: 107.

The sroE gene (synonym k20) encodes the SroE RNA (synonym k20). The sroE gene (nucleotides complementary to nucleotides in positions 2,638,617 to 2,638,708; GenBank accession no. NC_000913.2; gi: 49175990) is located between the hisS gene and the ispG gene on the chromosome of *E. coli* K-12. The nucleotide sequence of the sroE gene is shown in SEQ ID NO: 14.

The sroF gene (synonyms: ECK2554, b4441, tke1) encodes the SroF RNA. The sroF gene (nucleotides complementary to nucleotides in positions 2689362 to 2689214); GenBank accession no. NC_000913.2; gi: 49175990) is located between the yfhK ORF and the purL gene on the chromosome of *E. coli* K-12. The nucleotide sequence of the sroF gene is shown in SEQ ID NO: 108.

The sroG gene (synonym HB_456) encodes the SroG RNA. The sroG gene (nucleotides complemented to nucleotides in positions 3,182,592 to 3,182,740; GenBank accession no. NC_000913.2; gi: 49175990) is located between the ribB gene and the yqiC ORF on the chromosome of *E. coli* K-12. The nucleotide sequence of the sroG gene is shown in SEQ ID NO: 109.

The sroH gene encodes the SroH RNA. The sroH gene (nucleotides complemented to nucleotides in positions 4,188,350 to 4,188,510; GenBank accession no. NC_000913.2; gi: 49175990) is located between the htrC gene and the thiH gene, overlapping with the htrC gene, on the chromosome of *E. coli* K-12. The nucleotide sequence of the sroH gene is shown in SEQ ID NO: 110.

The ssrA gene (synonyms: ECK2617, b262, sipB) encodes the SsrA RNA. The ssrA gene (nucleotides in positions 2,753,615 to 2,753,977; GenBank accession no. NC_000913.2; gi: 49175990) is located between the smpB and intA genes on the chromosome of *E. coli* K-12. The nucleotide sequence of the ssrA gene is shown in SEQ ID NO: 111.

The ssrS gene (synonyms: ECK2906, b2911, ssr) encodes the SsrS RNA. The ssrS gene (nucleotides in positions 3,054,005 to 3,054,187; GenBank accession no. NC_000913.2; gi: 49175990) is located between the zapA gene and the ygfA ORF on the chromosome of *E. coli* K-12. The nucleotide sequence of the ssrS gene is shown in SEQ ID NO: 112.

The tff gene (synonyms: ECK0167, b4414, T44) encodes the tff RNA. The tff gene (nucleotides in positions 189,712 to 189,847; GenBank accession no. NC_000913.2; gi: 49175990) is located between the map gene and the rsp gene on the chromosome of *E. coli* K-12. The nucleotide sequence of the tff gene is shown in SEQ ID NO: 113.

The tp2 gene encodes the Tp2 RNA. The tp2 gene (nucleotides complemented to nucleotides in positions 122,697 to 122,857; GenBank accession no. NC_000913.2; gi: 49175990) is located between the pdhR gene and the aceE gene, overlapping with the pdhR gene, on the chromosome of *E. coli* K-12. The nucleotide sequence of the tp2 gene is shown in SEQ ID NO: 114.

The tpke11 gene encodes the Tpke11 RNA. The tpke11 gene (nucleotides complemented to nucleotides in positions 14,080 to 14,168; GenBank accession no. NC_000913.2; gi: 49175990) is located between the dnaK gene and the dnaJ gene on the chromosome of *E. coli* K-12. The nucleotide sequence of the tpke11 gene is shown in SEQ ID NO: 115.

The tpke70 gene encodes the Tp70 RNA. The tpke70 gene (nucleotides complementary to nucleotides in positions 2,494,216 to 2,494,651; GenBank accession no. NC_000913.2; gi: 49175990) is located between the lpxP gene and the yfdZ ORF, overlapping with the lpxP gene, on the chromosome of *E. coli* K-12. The nucleotide sequence of the tpke70 gene is shown in SEQ ID NO: 116.

Since there may be some differences in DNA sequences between the genera or strains of the Enterobacteriaceae family, the gene coding for sRNA is not limited to the genes shown in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 69-116, but may include genes homologous to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 69-116. Such a homologous gene may have homology that is enough to recombine a sRNA gene on the chromosome of a host bacterium.

Therefore, a gene coding for sRNA may be a variant which hybridizes under stringent conditions with a complement of the nucleotide sequence shown in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 69-116, or a probe which can be prepared from the nucleotide sequence, provided that it encodes a functional sRNA prior to inactivation, or provided that attenuation of expression of the gene in a host bacterium leads to improvement of L-amino acid-producing ability of the host bacterium. "Stringent conditions" include those under which a specific hybrid, for example, a hybrid having homology of not less than 80%, preferably not less than 90%, more preferably not less than 95%, still more preferably not less than 97%, and most preferably not less than 98%, is formed and a non-specific hybrid, for example, a hybrid having homology lower than the above, is not formed. For example, stringent conditions are exemplified by washing one time or more, preferably two or three times at a salt concentration of 1×SSC, 0.1% SDS, preferably 0.1×SSC, 0.1% SDS at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected, depending on the hybridization conditions, in this specific case it may be about 100 bp.

Homology between two amino acid sequences can be determined using the well-known methods, for example, the computer program BLAST 2.0.

Expression of a gene coding for sRNA can be attenuated by introducing a mutation into the gene on the chromosome so that the intracellular amount of the sRNA encoded by the gene is decreased as compared to an unmodified strain. Such a mutation can be introduction of insertion of a drug-resistance gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Nucleotide sequence information of the sRNA gene and its flanking regions can be obtained based on the accession number of each sRNA gene in Genbank. Expression of a gene coding for sRNA can also be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods may be employed to introduce a mutation by gene recombination. A mutant gene is prepared, and a bacterium is transformed with a DNA fragment containing the mutant gene. Then, the native gene on the chromosome is replaced with the mutant gene by homologous recombination, and the resulting strain is selected. Such gene replacement by homologous recombination can be conducted by employing a linear DNA, which is known as "Red-driven integration" (Datsenko, K. A. and Wanner, B. L., Proc. Natl. Acad. Sci. USA, 97, 12, p 6640-6645 (2000)), or by methods employing a plasmid containing a temperature-sensitive replication (U.S. Pat. No. 6,303,383 or JP 05-007491A). Furthermore, the incorporation of a site-specific mutation by gene substitution using homologous recombination such as set forth above can also be conducted with a plasmid lacking the ability to replicate in the host.

Expression of a gene can also be attenuated by insertion of a transposon or an IS factor into the coding region of the gene (U.S. Pat. No. 5,175,107), or by conventional methods, such as mutagenesis treatment using UV irradiation or nitrosoguanidine (N-methyl-N'-nitro-N-nitrosoguanidine) treatment.

The presence or absence of a gene coding for sRNA in the chromosome of a bacterium can be detected by well-known methods, including PCR, Southern blotting and the like. In addition, the level of gene expression can be estimated by measuring the amount of the RNA transcribed from the gene using various well-known methods, including Northern blotting, quantitative RT-PCR, and the like.

Methods for preparation of plasmid DNA, digestion and ligation of DNA, transformation, selection of an oligonucleotide as a primer, and the like may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

L-Amino Acid-Producing Bacteria

As a bacterium of the present invention which is modified to attenuate expression of a gene coding for sRNA, bacteria which are able to produce either an aromatic or a non-aromatic L-amino acids may be used. Examples of L-amino acid-producing bacteria are shown below.

The bacterium of the present invention can be obtained by attenuating expression of a gene coding for sRNA in a bacterium which inherently has the ability to produce L-amino acids. Alternatively, the bacterium of present invention can be obtained by imparting the ability to produce L-amino acids to a bacterium already having the attenuated expression of a gene coding for sRNA.

L-Threonine-Producing Bacteria

Examples of parent strains for deriving the L-threonine-producing bacteria of the present invention include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Russia, 117105 Moscow, Nagatinskaya Street 3-A) under the accession number RIA 1867. The strain was also deposited in the Russian National Collection of Industrial Microorganisms (VKPM) (Russia, 117545 Moscow, 1$^{st}$ Dorozhny proezd, 1) on Apr. 7, 1987 under the accession number VKPM B-3996.

*E. coli* VKPM B-5318 (EP 0593792B) may also be used as a parent strain for deriving L-threonine-producing bacteria of the present invention. The strain B-5318 is prototrophic with regard to isoleucine, and a temperature-sensitive lambda-phage C1 repressor and PR promoter replaces the regulatory region of the threonine operon in plasmid pVIC40. The strain VKPM B-5318 was deposited in the Russian National Collection of Industrial Microorganisms (VKPM) on May 3, 1990 under accession number of VKPM B-5318.

Preferably, the bacterium of the present invention is additionally modified to enhance expression of one or more of the following genes:

- the mutant thrA gene which codes for aspartokinase homoserine dehydrogenase I resistant to feed back inhibition by threonine;
- the thrB gene which codes for homoserine kinase;
- the thrC gene which codes for threonine synthase;
- the rhtA gene which codes for a putative transmembrane protein;
- the asd gene which codes for aspartate-β-semialdehyde dehydrogenase; and
- the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes functions as a single threonine operon. To enhance expression of the threonine operon, the attenuator region which affects the transcription is desirably removed from the operon (WO2005/049808, WO2003/097839).

A mutant thrA gene which codes for aspartokinase homoserine dehydrogenase I resistant to feed back inhibition by threonine, as well as, the thrB and thrC genes can be obtained as one operon from well-known plasmid pVIC40 which is presented in the threonine producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position −1 with respect to the ATG start codon (ABSTRACTS of the 17$^{th}$ International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC_000913.1, gi:16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine coexists in a medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346, 170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains for deriving L-lysine-producing bacteria of the present invention also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP 1253195 A). In addition, the parent strains may have an increased level of expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains for deriving L-lysine-producing bacteria of the present invention also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase (WO 95/23864), lysine decarboxylase (U.S. Pat. No. 5,827,698), and the malic enzyme (WO2005/010175).

L-Cysteine-Producing Bacteria

Examples of parent strains for deriving L-cysteine-producing bacteria of the present invention include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP11155571A2); *E. coli* W3110 with increased activity of a positive transcriptional regulator for cysteine regulon encoded by the cysB gene (W00127307 A1), and the like.

L-Leucine-Producing Bacteria

Examples of parent strains for deriving L-leucine-producing bacteria of the present invention include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium of the present invention may be improved by enhancing the expression of one or more genes involved in L-leucine biosynthesis. Examples include genes of the leuABCD operon, which are preferably represented by a mutant leuA gene coding for isopropylmalate synthase freed from feedback inhibition by L-leucine (U.S. Pat. No. 6,403, 342). In addition, the bacterium of the present invention may be improved by enhancing the expression of one or more genes coding for proteins which excrete L-amino acid from the bacterial cell. Examples of such genes include the b2682 and b2683 genes (ygaZH genes) (EP 1239041 A2).

L-Histidine-Producing Bacteria

Examples of parent strains for deriving L-histidine-producing bacteria of the present invention include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554) and the like.

Examples of parent strains for deriving L-histidine-producing bacteria of the present invention also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase (Russian Patent Nos. 2003677 and 2119536).

Specific examples of strains having an L-histidine-producing ability include *E. coli* FERM-P 5038 and 5048 which have been introduced with a vector carrying a DNA encoding an L-histidine-biosynthetic enzyme (JP 56-005099 A), *E. coli* strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains for deriving L-glutamic acid-producing bacteria of the present invention include, but are not limited to, strains belonging to the genus *Escherichia*, such as *E. coli* VL334thrC⁺ (EP 1172433). *E. coli* VL334

(VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC⁺ (VKPM B-8961), which is able to produce L-glutamic acid, was obtained.

Examples of parent strains for deriving the L-glutamic acid-producing bacteria of the present invention include, but are not limited to, strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains for deriving the L-glutamic acid-producing bacteria of the present invention also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

E. coli W3110sucA::Km$^R$
E. coli AJ12624 (FERM BP-3853)
E. coli AJ12628 (FERM BP-3854)
E. coli AJ12949 (FERM BP-4881)

*E. coli* W3110sucA::Km$^R$ is a strain obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in the α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria include mutant strains belonging to the genus *Pantoea* which are deficient in α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in the α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Phenylalanine-Producing Bacteria

Examples of parent strains for deriving L-phenylalanine-producing bacteria of the present invention include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the mutant pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-Tryptophan-Producing Bacteria

Examples of parent strains for deriving the L-tryptophan-producing bacteria of the present invention include, but are not limited to, strains belonging to the genus *Escherichia*, such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614); *E. coli* AGX17/pGX50, pACKG4-pps in which a phosphoenolpyruvate-producing ability is enhanced (WO9708333, U.S. Pat. No. 6,319,696), and the like may be used. L-tryptophan-producing bacteria belonging to the genus *Escherichia* with an enhanced activity of the identified protein encoded by the yedA gene or the yddG gene may also be used (U.S. patent applications 2003/0148473 A1 and 2003/0157667 A1).

Examples of parent strains for deriving the L-tryptophan-producing bacteria of the present invention also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include an *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains for deriving the L-tryptophan-producing bacteria of the present invention also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Proline-Producing Bacteria

Examples of parent strains for deriving L-proline-producing bacteria of the present invention include, but are not limited to, strains belonging to the genus *Escherichia*, such as *E. coli* 702ilvA (VKPM B-8012) which is deficient in the ilvA gene and is able to produce L-proline (EP 1172433). The bacterium of the present invention may be improved by enhancing the expression of one or more genes involved in L-proline biosynthesis. Examples of such genes for L-proline producing bacteria which are preferred include the proB gene coding for glutamate kinase of which feedback inhibition by L-proline is desensitized (DE Patent 3127361). In addition, the bacterium of the present invention may be improved by enhancing the expression of one or more genes coding for proteins excreting L-amino acid from bacterial cell. Such genes are exemplified by b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-Arginine-Producing Bacteria

Examples of parent strains for deriving L-arginine-producing bacteria of the present invention include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthetase is introduced therein (EP1170361A1), and the like.

Examples of parent strains for deriving L-arginine producing bacteria of the present invention also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Examples of parent strains for deriving L-valine-producing bacteria of the present invention include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by L-valine that is produced. Furthermore, the ilvA gene in the operon is desirably disrupted so that threonine deaminase activity is decreased.

Examples of parent strains for deriving L-valine-producing bacteria of the present invention include also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 117545 Moscow, 1$^{st}$ Dorozhny Proezd, 1) on Jun. 24, 1988 under accession number VKPM B-4411.

Furthermore, mutants requiring lipoic acid for growth and/or lacking H$^+$-ATPase can also be used as parent strains (WO96/06926).

L-Isoleucine-Producing Bacteria

Examples of parent strains for deriving L-isoleucine producing bacteria of the present invention include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

2. Method of the Present Invention

The method of the present invention is a method for producing an L-amino acid comprising cultivating the bacterium of the present invention in a culture medium to produce and excrete the L-amino acid into the medium, and collecting the L-amino acid from the medium.

The cultivation, collection, and purification of an L-amino acid from the medium and the like may be performed in a manner similar to conventional fermentation methods wherein an amino acid is produced using a bacterium.

The medium used for culture may be either synthetic or natural, so long as it includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as a shaking culture, and a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting Examples.

Example 1

Construction of a Strain with an Inactivated Gene Coding for sRNA

1. Deletion of a Target Gene

A strain having deletion of a gene coding for sRNA can be constructed by the method initially developed by Datsenko, K. A. and Wanner, B. L. (Proc. Natl. Acad. Sci. USA, 2000, 97 (12), 6640-6645) called "Red-driven integration". The DNA fragment containing the $Cm^R$ marker encoded by the cat gene can be obtained by PCR, using primers P1 (upstream primer) and P2 (downstream primer) and plasmid pMW118-attL-Cm-attR (WO 05/010175) as a template. Primer P1 contains both a region complementary to the 35/36-nt region located at the 3' end of a target gene and a region complementary to the attL region in the plasmid pMW118-attL-Cm-attR. Primer P2 contains both a region complementary to the 35/36-nt region located at the 5' end of a target gene and a region complementary to the attR region in the plasmid pMW118-attL-Cm-attR. The nucleotide sequences of the region complementary to the attL region in the plasmid pMW118-attL-Cm-attR and the region complementary to the attR region in the plasmid pMW118-attL-Cm-attR are shown in SEQ ID NO: 15 and SEQ ID NO: 16, respectively.

Conditions for PCR can be as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

A PCR product (FIG. 1) can be obtained and purified in an agarose gel and can be used for electroporation of the E. coli strain MG1655 (ATCC 700926), which contains the plasmid pKD46 having a temperature-sensitive replication. The plasmid pKD46 (Datsenko, K. A. and Wanner, B. L., Proc. Natl. Acad. Sci. USA, 2000, 97:12:6640-45) includes a 2,154 nucleotide DNA fragment of phage λ (nucleotide positions 31088 to 33241, GenBank accession no. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655.

Electrocompetent cells can be prepared as follows: E. coli MG1655/pKD46 can be grown overnight at 30° C. in LB medium containing ampicillin (100 mg/l), and the culture can be diluted 100 times with 5 ml of SOB medium (Sambrook et al, "Molecular Cloning: A Laboratory Manual, Second Edition", Cold Spring Harbor Laboratory Press, 1989) containing ampicillin and L-arabinose (1 mM). The cells can be grown with aeration at 30° C. to an $OD_{600}$ of ≈0.6 and then can be made electrocompetent by concentrating 100-fold and washing three times with ice-cold deionized $H_2O$. Electroporation can be performed using 70 μl of cells and ≈100 ng of the PCR product. Cells after electroporation can be incubated with 1 ml of SOC medium (Sambrook et al, "Molecular Cloning: A Laboratory Manual, Second Edition", Cold Spring Harbor Laboratory Press, 1989) at 37° C. for 2.5 hours and then can be plated onto L-agar containing chloramphenicol (30 μg/ml) and grown at 37° C. to select $Cm^R$ recombinants. Then, to eliminate the pKD46 plasmid, two passages on L-agar with Cm at 42° C. can be performed and the colonies can be tested for sensitivity to ampicillin.

2. Verification of a Target Gene Deletion by PCR

Figure 2:
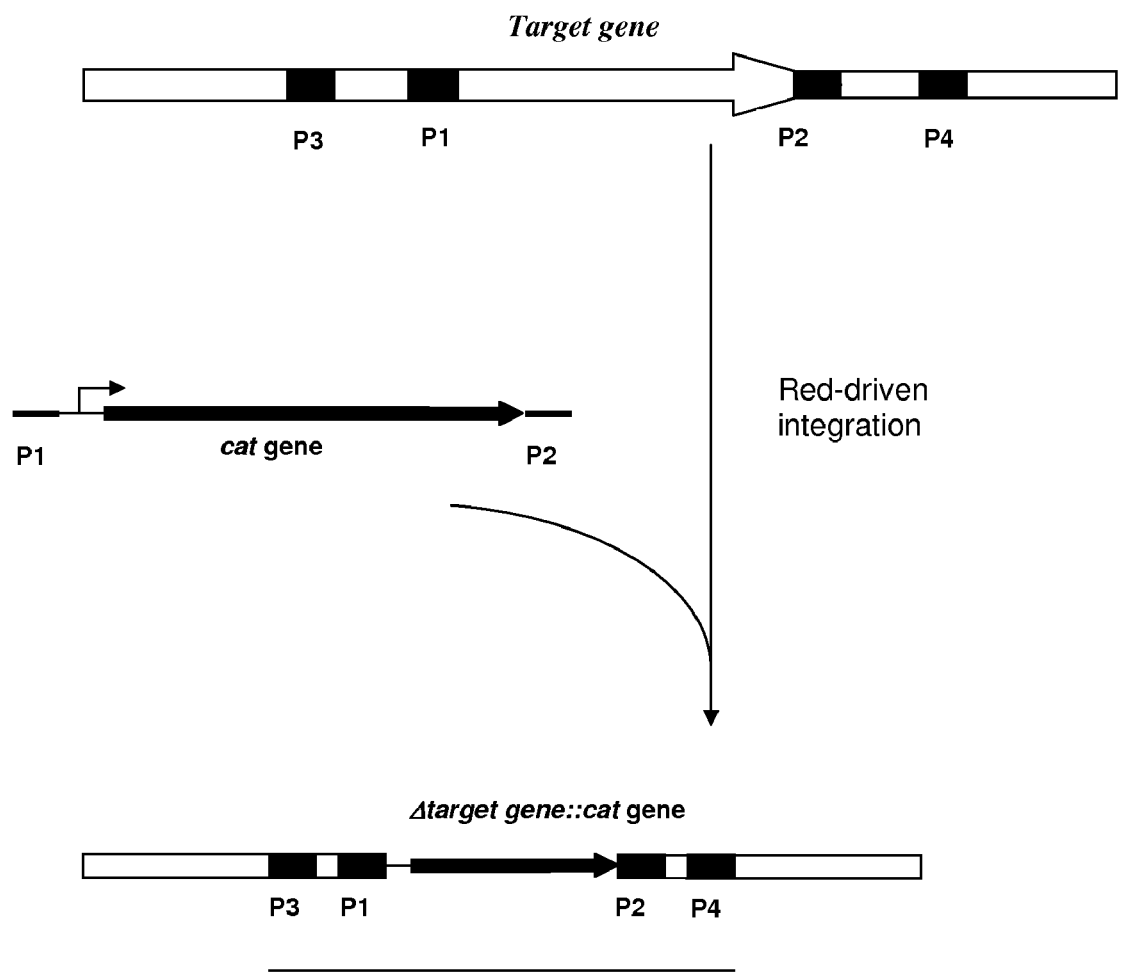
FIG. 2 shows the construction of the chromosomal DNA fragment containing the inactivated target gene.

The mutants having a gene coding for sRNA deleted and marked with the Cm resistance gene can be verified by PCR. Locus-specific primers P3 and P4 can be used in PCR for the verification. Conditions for PCR verification can be as follows: denaturation step for 3 min at 94° C.; profile for 30 cycles: 30 sec at 94° C., 30 sec at 54° C., 1 min at 72° C.; final step: 7 min at 72° C. The PCR product obtained in the reaction with the cells of parental strain MG1655 as a template and the PCR product obtained in the reaction with the cells of mutant strain as the template should differ in length (FIG. 2). Mutant E. coli MG1655 having a gene coding for sRNA (target gene) deleted and marked with the Cm resistance gene can be obtained in this manner.

3. Construction of Strains with Inactivated c0362, c0465, dsrA, gcvB, micC, rprA, rybB, ryeE, rygB-sraE, sraA, sraB, sraH and sroE Genes Strains having deletion of c0362, c0465, dsrA, gcvB, micC, rprA, rybB, ryeE, rygB-sraE, sraA, sraB, sraH and sroE genes were constructed by the described above method. The nucleotide sequences of primers P1 (upstream primer) and P2 (downstream primer) used for PCR amplification of the cat gene are shown in Table 1. The mutants having the target gene deleted and marked with the Cm resistance gene, constructed as a result of electroporation of E. coli strain MG1655 with 1699-bp PCR product, elimination the pKD46 plasmid and selection of mutants, were verified by PCR. Locus-specific primers P3 and P4 used in PCR for the verification as well as lengths of PCR products obtained in the reactions with the cells of parental strain MG1655 and mutant strains as templates are shown in Table 1.

The mutant strains having deletion of c0362, c0465, dsrA, gcvB, micC, rprA, rybB, ryeE, rygB-sraE, sraA, sraB, sraH and sroE genes were named MG1655 Δc0362::cat, MG1655 Δc0465::cat, MG1655 ΔdsrA::cat, MG1655 ΔgcvB::cat, MG1655 ΔmicC::cat, MG1655 ΔrprA::cat, MG1655 ΔrybB::cat, MG1655 ΔryeE::cat, MG1655 ΔrygB-sraE::cat, MG1655 ΔsraA::cat, MG1655 ΔsraB::cat, MG1655 ΔsraH::cat and MG1655 ΔsroE::cat, respectively.

TABLE 1

| Target gene | SEQ ID of upstream (P1) and downstream (P2) primers for the target gene deletion | SEQ ID of P3 and P4 primers for verification of the target gene deletion | Length of PCR product obtained using as a template chromosome of: | |
|---|---|---|---|---|
| | | | parental strain | mutant strain |
| c0362 | P1-SEQ ID NO: 17<br>P2-SEQ ID NO: 18 | P3-SEQ ID NO: 19<br>P4-SEQ ID NO: 20 | ~0.7 kb | ~2.0 kb |
| c0465 | P1-SEQ ID NO: 21<br>P2-SEQ ID NO: 22 | P3-SEQ ID NO: 23<br>P4-SEQ ID NO: 24 | ~0.3 kb | ~1.9 kb |
| dsrA | P1-SEQ ID NO: 25<br>P2-SEQ ID NO: 26 | P3-SEQ ID NO: 27<br>P4-SEQ ID NO: 28 | ~0.4 kbp | ~2.0 kbp |
| gcvB | P1-SEQ ID NO: 29<br>P2-SEQ ID NO: 30 | P3-SEQ ID NO: 31<br>P4-SEQ ID NO: 32 | ~0.5 kbp | ~2.0 kbp |
| micC | P1-SEQ ID NO: 33<br>P2-SEQ ID NO: 34 | P3-SEQ ID NO: 35<br>P4-SEQ ID NO: 36 | ~0.3 kbp | ~1.9 kbp |
| rprA | P1-SEQ ID NO: 37<br>P2-SEQ ID NO: 38 | P3-SEQ ID NO: 39<br>P4-SEQ ID NO: 40 | ~0.4 kbp | ~1.9 kbp |
| rybB | P1-SEQ ID NO: 41<br>P2-SEQ ID NO: 42 | P3-SEQ ID NO: 43<br>P4-SEQ ID NO: 44 | ~0.5 kbp | ~2.1 kbp |
| ryeE | P1-SEQ ID NO: 45<br>P2-SEQ ID NO: 46 | P3-SEQ ID NO: 47<br>P4-SEQ ID NO: 48 | ~0.5 kbp | ~2.2 kbp |
| rygB-sraE | P1-SEQ ID NO: 49<br>P2-SEQ ID NO: 50 | P3-SEQ ID NO: 51<br>P4-SEQ ID NO: 52 | ~0.5 kbp | ~1.9 kbp |
| sraA | P1-SEQ ID NO: 53<br>P2-SEQ ID NO: 54 | P3-SEQ ID NO: 55<br>P4-SEQ ID NO: 56 | ~0.3 kbp | ~1.9 kbp |
| sraB | P4-SEQ ID NO: 57<br>P2-SEQ ID NO: 58 | P3-SEQ ID NO: 59<br>P4-SEQ ID NO: 60 | ~0.4 kbp | ~2.0 kbp |
| sraH | P1-SEQ ID NO: 61<br>P2-SEQ ID NO: 62 | P3-SEQ ID NO: 63<br>P4-SEQ ID NO: 64 | ~0.5 kbp | ~2.1 kbp |
| sroE | P1-SEQ ID NO: 65<br>P2-SEQ ID NO: 66 | P3-SEQ ID NO: 67<br>P4-SEQ ID NO: 68 | ~0.3 kbp | ~1.9 kbp |

Example 2

Production of L-Threonine by *E. Coli* Strain Having a Gene Coding for sRNA Deleted To test the effect of inactivation of a gene coding for sRNA on threonine production, DNA fragments from the chromosome of the above-described mutant *E. coli* MG1655 having a gene coding for sRNA (target gene) deleted and marked with the Cm resistance gene can be transferred to the threonine-producing *E. coli* strain VKPM B-3996 by P1 transduction (Miller, J. H. Experiments in Molecular Genetics, Cold Spring Harbor Lab. Press, 1972, Plainview, N.Y.) to obtain strain B-3996-Δtarget gene. The strain B-3996 was deposited on Nov. 19, 1987 in the All-Union Scientific Center of Antibiotics (Russia, 117105 Moscow, Nagatinskaya Street, 3-A) under the accession number RIA 1867. The strain was also deposited in the Russian National Collection of Industrial Microorganisms (VKPM) (Russia, 117545 Moscow, 1$^{st}$ Dorozhny proezd, 1) on Apr. 7, 1987 under the accession number B-3996. The strains B-3996-Δc0362, B-3996-Δc0465, B-3996-ΔdsrA, B-3996-ΔgcvB, B-3996-ΔmicC, B-3996-ΔrprA, B-3996-ΔrybB, B-3996-ΔryeE, B-3996-ΔrygB-sraE, B-3996-ΔsraB and B-3996-ΔsraH were obtained in this manner.

Strains B-3996 and each of strains B-3996-Δc0362, B-3996-Δc0465, B-3996-ΔdsrA, B-3996-ΔgcvB, B-3996-ΔmicC, B-3996-ΔrprA, B-3996-ΔrybB, B-3996-ΔryeE, B-3996-ΔrygB-sraE, B-3996-ΔsraB or B-3996-ΔsraH, were separately grown for 18-24 hours at 37° C. on L-agar plates. To obtain a seed culture, the strains were grown on a rotary shaker (250 rpm) at 32° C. for 18 hours in 20×200-mm test tubes containing 2 ml of L-broth supplemented with 4% glucose. Then, the fermentation medium was inoculated with 0.21 ml (10%) of seed material. The fermentation was performed in 2 ml of minimal medium for fermentation in 20×200-mm test tubes. Cells were grown for 65 hours at 32° C. with shaking at 250 rpm.

After cultivation, the amount of L-threonine which had accumulated in the medium, was determined by paper chromatography using the following mobile phase: butanol-acetic acid-water=4:1:1 (v/v). A solution of ninhydrin (2%) in acetone was used as a visualizing reagent. A spot containing L-threonine was cut out, L-threonine was eluted with 0.5% water solution of $CdCl_2$, and the amount of L-threonine was estimated spectrophotometrically at 540 nm. The results of ten (for B-3996-ΔdsrA, 3996-ΔrprA and B-3996-ΔsraB)/eight (for B-3996-Δc0362, B-3996-Δc0465, B-3996-ΔgcvB, B-3996-ΔryeE, B-3996-ΔrygB-sraE and B-3996-ΔsraH)/five (for B-3996-ΔmicC and B-3996-ΔrybB) independent test tube fermentations are shown in Table 2. As follows from Table 2, B-3996-Δc0362, B-3996-Δc0465, B-3996-ΔdsrA, B-3996-ΔgcvB, B-3996-ΔmicC, B-3996-ΔrprA, B-3996-ΔrybB, B-3996-ΔryeE, B-3996-ΔrygB-sraE, B-3996-ΔsraB and B-3996-ΔsraH produced a higher amount of L-threonine, as compared to B-3996.

TABLE 2

| Strain | $OD_{540}$ | Amount of L-threonine, g/l |
|---|---|---|
| B-3996 | 24.6 ± 0.6 | 24.7 ± 0.3 |
| B-3996-Δc0362 | 24.7 ± 0.7 | 26.8 ± 1.6 |
| B-3996 | 29.5 ± 0.5 | 27.3 ± 0.2 |
| B-3996-Δc0465 | 29.4 ± 0.7 | 27.6 ± 0.6 |
| B-3996 | 25.0 ± 1.1 | 29.0 ± 0.4 |
| B-3996-ΔgcvB | 25.0 ± 0.5 | 31.0 ± 0.7 |
| B-3996 | 28.3 ± 0.3 | 27.6 ± 0.7 |
| B-3996-ΔsraB | 29.7 ± 0.6 | 28.5 ± 0.7 |
| B-3996 | 32.8 ± 0.9 | 21.1 ± 0.3 |
| B-3996-ΔdsrA | 32.2 ± 0.5 | 21.9 ± 0.6 |

TABLE 2-continued

| Strain | OD$_{540}$ | Amount of L-threonine, g/l |
|---|---|---|
| B-3996 | 22.9 ± 1.5 | 25.5 ± 0.5 |
| B-3996-ΔrybB | 18.5 ± 2.0 | 26.7 ± 0.5 |
| B-3996 | 29.4 ± 0.7 | 25.9 ± 0.7 |
| B-3996-ΔrygB-sraE | 30.3 ± 1.2 | 28.0 ± 1.1 |
| B-3996-ΔryeE | 28.5 ± 1.0 | 28.0 ± 1.0 |
| B-3996-ΔsraH | 29.9 ± 1.2 | 27.1 ± 0.9 |
| B-3996 | 24.4 ± 0.4 | 26.8 ± 0.5 |
| B-3996-ΔrprA | 24.5 ± 1.2 | 27.6 ± 0.9 |
| B-3996 | 19.3 ± 0.8 | 20.2 ± 0.9 |
| B-3996-ΔmicC | 19.8 ± 0.9 | 24.3 ± 1.4 |

The composition of the fermentation medium (g/l) was as follows:

| Glucose | 80.0 |
|---|---|
| (NH$_4$)$_2$SO$_4$ | 22.0 |
| NaCl | 0.8 |
| KH$_2$PO$_4$ | 2.0 |
| MgSO$_4$7H$_2$O | 0.8 |
| FeSO$_4$7H$_2$O | 0.02 |
| MnSO$_4$5H$_2$O | 0.02 |
| Thiamine HCl | 0.0002 |
| Yeast extract | 1.0 |
| CaCO$_3$ | 30.0 |

Glucose and magnesium sulfate were sterilized separately. CaCO$_3$ was sterilized by dry-heat at 180° C. for 2 hours. The pH was adjusted to 7.0. The antibiotic was introduced into the medium after sterilization.

Example 3

Production of L-Lysine by *E. coli* Strain Having a Gene Coding for sRNA Deleted To test the effect of inactivation of a gene coding for sRNA on lysine production, DNA fragments from the chromosome of the above-described mutant *E. coli* MG1655 having a gene coding for sRNA (target gene) deleted and marked with the Cm resistance gene can be transferred to the lysine-producing *E. coli* strain AJ11442 by P1 transduction (Miller, J. H. Experiments in Molecular Genetics, Cold Spring Harbor Lab. Press, 1972, Plainview, N.Y.) to obtain strain AJ11442-Δtarget gene. AJ11442 strain was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on May 1, 1981 and received an accession number of FERM BP-1543. Both *E. coli* strains, AJ11442 and AJ11442-Δtarget gene, can be cultured in L-medium at 37° C., and 0.3 ml of the obtained culture can be inoculated into 20 ml of the fermentation medium containing the required drugs in a 500-ml flask. The cultivation can be carried out at 37° C. for 16 h by using a reciprocal shaker at the agitation speed of 115 rpm. After the cultivation, the amounts of L-lysine and residual glucose in the medium can be measured by a known method (Biotech-analyzer AS210 manufactured by Sakura Seiki Co.). Then, the yield of L-lysine can be calculated relative to consumed glucose for each of the strains.

The composition of the fermentation medium (g/l) is as follows:

| Glucose | 40 |
|---|---|
| (NH$_4$)$_2$SO$_4$ | 24 |
| K$_2$HPO$_4$ | 1.0 |
| MgSO$_4$7H$_2$O | 1.0 |
| FeSO$_4$7H$_2$O | 0.01 |
| MnSO$_4$5H$_2$O | 0.01 |
| Yeast extract | 2.0 |

The pH is adjusted to 7.0 by KOH and the medium is autoclaved at 115° C. for 10 min. Glucose and MgSO$_4$7H$_2$O are sterilized separately. CaCO$_3$ is dry-heat sterilized at 180° C. for 2 hours and added to the medium for a final concentration of 30 g/l.

Example 4

Production of L-Cysteine by *E. coli* Strain Having a Gene Coding for sRNA Deleted To test the effect of inactivation of a gene coding for sRNA on L-cysteine production, DNA fragments from the chromosome of the above-described mutant *E. coli* MG1655 having a gene coding for sRNA (target gene) deleted and marked with the Cm resistance gene can be transferred to the *E. coli* L-cysteine-producing strain JM15(ydeD) by P1 transduction (Miller, J. H. Experiments in Molecular Genetics, Cold Spring Harbor Lab. Press, 1972, Plainview, N.Y.) to obtain the strain JM15(ydeD)-Δtarget gene.

*E. coli* strain JM15(ydeD) is a derivative of *E. coli* strain JM15 (U.S. Pat. No. 6,218,168) which can be transformed with DNA having the ydeD gene, which codes for a membrane protein, and is not involved in a biosynthetic pathway of any L-amino acid (U.S. Pat. No. 5,972,663, US2005-0124049). The strain JM15 (CGSC# 5042) can be obtained from The Coli Genetic Stock Collection at the *E. coli* Genetic Resource Center, MCD Biology Department, Yale University (http://cgsc.biology.yale.edu/).

Fermentation conditions for evaluation of L-cysteine production were described in detail in Example 6 of U.S. Pat. No. 6,218,168.

Example 5

Production of L-Leucine by *E. Coli* Strain Having a Gene Coding for sRNA Deleted To test the effect of inactivation of a gene coding for sRNA on L-leucine production, DNA fragments from the chromosome of the above-described mutant *E. coli* MG1655 having a gene coding for sRNA (target gene) deleted and marked with the Cm resistance gene can be transferred to the *E. coli* L-leucine-producing strain 57 (VKPM B-7386, U.S. Pat. No. 6,124,121) by P1 transduction (Miller, J. H. Experiments in Molecular Genetics, Cold Spring Harbor Lab. Press, 1972, Plainview, N.Y.) to obtain the strain 57-Δtarget gene. The strain 57 has been deposited in the Russian National Collection of Industrial Microorganisms (VKPM) (Russia, 117545 Moscow, 1$^{st}$ Dorozhny proezd, 1) on May 19, 1997 under accession number VKPM B-7386.

Both *E. coli* strains, 57 and 57-Δtarget gene, can be cultured for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% sucrose. Then, the fermentation medium can be inoculated with 0.21 ml of seed material (10%). The fermentation can be performed in 2 ml of a minimal fermentation medium in 20×200-mm test tubes. Cells can be grown for 48-72 hours at 32° C. with shaking at 250 rpm. The amount of L-leucine can be measured by paper chromatography (liquid phase composition: butanol-acetic Acid-water=4:1:1).

The composition of the fermentation medium (g/l) (pH 7.2) is as follows:

| | |
|---|---|
| Glucose | 60.0 |
| $(NH_4)_2SO_4$ | 25.0 |
| $K_2HPO_4$ | 2.0 |
| $MgSO_4 7H_2O$ | 1.0 |
| Thiamine | 0.01 |
| $CaCO_3$ | 25.0 |

Glucose and $CaCO_3$ are sterilized separately.

Example 6

Production of L-Histidine by *E. coli* Strain Having a Gene Coding for sRNA Deleted To test the effect of inactivation of a gene coding for sRNA on L-histidine production, DNA fragments from the chromosome of the above-described mutant *E. coli* MG1655 having a gene coding for sRNA (target gene) deleted and marked with the Cm resistance gene can be transferred to the histidine-producing *E. coli* strain 80 by P1 transduction (Miller, J. H. Experiments in Molecular Genetics, Cold Spring Harbor Lab. Press, 1972, Plainview, N.Y.) to obtain strain 80-Δtarget gene. The strain 80 has been described in Russian patent 2119536 and deposited in the Russian National Collection of Industrial Microorganisms (Russia, 117545 Moscow, 1st Dorozhny proezd, 1) on Oct. 15, 1999 under accession number VKPM B-7270 and then converted to a deposit under the Budapest Treaty on Jul. 12, 2004.

Both *E. coli* strains, 80 and 80-Δtarget gene, can each be cultured in L-broth for 6 h at 29° C. Then, 0.1 ml of obtained culture can be inoculated into 2 ml of fermentation medium in a 20×200-mm test tube and cultivated for 65 hours at 29° C. with shaking on a rotary shaker (350 rpm). After cultivation, the amount of histidine which accumulates in the medium can be determined by paper chromatography. The paper can be developed with a mobile phase consisting of n-butanol:acetic acid:water=4:1:1 (v/v). A solution of ninhydrin (0.5%) in acetone can be used as a visualizing reagent.

The composition of the fermentation medium (g/l) is as follows (pH 6.0):

| | |
|---|---|
| Glucose | 100.0 |
| Mameno (soybean hydrolysate) | 0.2 of as total nitrogen |
| L-proline | 1.0 |
| $(NH_4)_2SO_4$ | 25.0 |
| $KH_2PO_4$ | 2.0 |
| $MgSO_4 7H_2O$ | 1.0 |
| $FeSO_4 7H_2O$ | 0.01 |
| $MnSO_4$ | 0.01 |
| Thiamine | 0.001 |
| Betaine | 2.0 |
| $CaCO_3$ | 60.0 |

Glucose, proline, betaine and $CaCO_3$ are sterilized separately. The pH is adjusted to 6.0 before sterilization.

Example 7

Production of L-Glutamate by *E. coli* Strain Having a Gene Coding for sRNA Deleted To test the effect of inactivation of a gene coding for sRNA on L-glutamate production, DNA fragments from the chromosome of the above-described mutant *E. coli* MG1655 having a gene coding for sRNA (target gene) deleted and marked with the Cm resistance gene can be transferred to the *E. coli* L-glutamate-producing strain VL334thrC$^+$ (EP 1172433) by P1 transduction (Miller, J. H. Experiments in Molecular Genetics, Cold Spring Harbor Lab. Press, 1972, Plainview, N.Y.) to obtain the strain VL334thrC$^+$-Δtarget gene. The strain VL334thrC$^+$ has been deposited in the Russian National Collection of Industrial Microorganisms (VKPM) (Russia, 117545 Moscow, 1$^{st}$ Dorozhny proezd, 1) on Dec. 6, 2004 under the accession number VKPM B-8961 and then converted to a deposit under the Budapest Treaty on Dec. 8, 2004.

Both strains, VL334thrC$^+$ and VL334thrC-Δtarget gene, can be grown for 18-24 hours at 37° C. on L-agar plates. Then, one loop of the cells can be transferred into test tubes containing 2 ml of fermentation medium. The fermentation medium contains glucose (60 g/l), ammonium sulfate (25 g/l), $KH_2PO_4$ (2 g/l), $MgSO_4$ (1 g/l), thiamine (0.1 mg/ml), L-isoleucine (70 µg/ml), and $CaCO_3$ (25 g/l). The pH is adjusted to 7.2. Glucose and $CaCO_3$ are sterilized separately. Cultivation can be carried out at 30° C. for 3 days with shaking. After the cultivation, the amount of L-glutamic acid which is produced can be determined by paper chromatography (liquid phase composition of butanol-acetic acid-water=4:1:1) with subsequent staining by ninhydrin (1% solution in acetone) and further elution of the compounds in 50% ethanol with 0.5% $CdCl_2$.

Example 8

Production of L-Phenylalanine by *E. coli* Strain Having a Gene Coding for sRNA Deleted To test the effect of inactivation of a gene coding for sRNA on L-phenylalanine production, DNA fragments from the chromosome of the above-described mutant *E. coli* MG1655 having a gene coding for sRNA (target gene) deleted and marked with the Cm resistance gene can be transferred to the phenylalanine-producing *E. coli* strain AJ12739 by P1 transduction (Miller, J. H. Experiments in Molecular Genetics, Cold Spring Harbor Lab. Press, 1972, Plainview, N.Y.) to obtain strain AJ12739-Δtarget gene. The strain AJ12739 has been deposited in the Russian National Collection of Industrial Microorganisms (VKPM) (Russia, 117545 Moscow, 1$^{st}$ Dorozhny proezd, 1) on Nov. 6, 2001 under accession no. VKPM B-8197 and then converted to a deposit under the Budapest Treaty on Aug. 23, 2002.

Both strains, AJ12739-Δtarget gene and AJ12739, can be cultivated at 37° C. for 18 hours in a nutrient broth, and 0.3 ml of the obtained culture can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol:ethylacetate:25% aqueous ammonia:water=40:40:7:16 (v/v). A solution of ninhydrin (2%) in acetone can be used as a visualizing reagent.

The composition of the fermentation medium (g/l) is as follows:

| | |
|---|---|
| Glucose | 40.0 |
| $(NH_4)_2SO_4$ | 16.0 |
| $K_2HPO_4$ | 0.1 |
| $MgSO_4 7H_2O$ | 1.0 |
| $FeSO_4 7H_2O$ | 0.01 |
| $MnSO_4 5H_2O$ | 0.01 |
| Thiamine HCl | 0.0002 |
| Yeast extract | 2.0 |
| Tyrosine | 0.125 |
| $CaCO_3$ | 20.0 |

Glucose and magnesium sulfate are sterilized separately. $CaCO_3$ is dry-heat sterilized at 180° for 2 hours. The pH is adjusted to 7.0.

Example 9

Production of L-Tryptophan by *E. coli* Strain Having a Gene Coding for sRNA Deleted To test the effect of inactivation of a gene coding for sRNA on L-tryptophan production, DNA fragments from the chromosome of the above-described mutant *E. coli* MG1655 having a gene coding for sRNA (target gene) deleted and marked with the Cm resistance gene can be transferred to the tryptophan-producing *E. coli* strain SV164 (pGH5) by P1 transduction (Miller, J. H. Experiments in Molecular Genetics, Cold Spring Harbor Lab. Press, 1972, Plainview, N.Y.) to obtain the strain SV164 (pGH5)-Δtarget gene. The strain SV164 has the trpE allele encoding anthranilate synthase free from feedback inhibition by tryptophan. The plasmid pGH5 harbors a mutant serA gene encoding phosphoglycerate dehydrogenase free from feedback inhibition by serine. The strain SV164 (pGH5) was described in detail in U.S. Pat. No. 6,180,373 or European patent 0662143. The strains SV164 (pGH5)-ΔgcvB::cat, SV164 (pGH5) ΔrprA::cat, SV164 (pGH5)-ΔsraA::cat, SV164 (pGH5)-ΔsraB::cat, SV164 (pGH5)-ΔsraH::cat and SV164 (pGH5)-ΔsroE::cat were obtained in this manner.

Strains SV164 (pGH5) and each of strains SV164 (pGH5)-ΔgcvB::cat, SV164 (pGH5)-ΔrprA::cat, SV164 (pGH5)-ΔsraA::cat, SV164 (pGH5)-ΔsraB::cat, SV164 (pGH5)-ΔsraH::cat or SV164 (pGH5)-ΔsroE::cat, were separately cultivated with shaking at 32° C. for 18 hours in 3 ml of nutrient broth supplemented with tetracycline (10 mg/ml, marker of pGH5 plasmid). The obtained cultures (0.3 ml each) were inoculated into 3 ml of a fermentation medium containing tetracycline (10 mg/ml) in 20×200-mm test tubes, and cultivated at 32° C. for 72 hours with a rotary shaker at 250 rpm. After cultivation, the amount of tryptophan which accumulates in the medium was determined by TLC as described in Example 8. The results of ten (for SV164 (pGH5)-ΔgcvB::cat, SV164 (pGH5)-ΔrprA::cat and SV164 (pGH5)-ΔsraB::cat)/seven (for SV164 (pGH5)-ΔsraA::cat and SV164 (pGH5)-ΔsraH::cat)/five (for SV164 (pGH5)-ΔsroE::cat) independent test tube fermentations are shown in Table 4. As follows from Table 4, SV164 (pGH5)-ΔgcvB::cat, SV164 (pGH5)-ΔrprA::cat, SV164 (pGH5)-ΔsraA::cat, SV164 (pGH5)-ΔsraB::cat, SV164 (pGH5)-ΔsraH::cat and SV164 (pGH5)-ΔsroE::cat produced a higher amount of L-tryptophan, as compared to SV164 (pGH5).

TABLE 4

| Strain | $OD_{540}$ | Amount of L-tryptophane, g/l |
|---|---|---|
| SV164/pGH5 | 34.6 ± 1.6 | 4.1 ± 0.1 |
| SV164/pGH5-ΔrprA | 34.8 ± 1.4 | 4.4 ± 0.4 |
| SV164/pGH5-ΔsraB | 32.9 ± 0.9 | 4.6 ± 0.5 |
| SV164 (pGH5) | 38.5 ± 0.3 | 3.9 ± 0.4 |
| SV164 (pGH5)-ΔsraH | 34.1 ± 1.1 | 4.3 ± 0.9 |
| SV164 (pGH5) | 34.2 ± 1.8 | 3.3 ± 0.3 |
| SV164 (pGH5)-ΔsraA | 23.3 ± 1.2 | 3.8 ± 0.6 |
| SV164 (pGH5) | 28.6 ± 0.5 | 6.3 ± 0.2 |
| SV164 (pGH5)-ΔsroE | 26.3 ± 1.1 | 6.6 ± 0.1 |
| SV164 (pGH5)-ΔgcvB | 28.7 ± 0.5 | 6.6 ± 0.2 |

The fermentation medium components are listed in Table 3, but should be sterilized in separate groups (A, B, C, D, E, F, and G), as shown, to avoid adverse interactions during sterilization.

TABLE 3

| Solutions | Component | Final concentration, g/l |
|---|---|---|
| A | $KH_2PO_4$ | 0.28 |
| | NaCl | 0.14 |
| | $(NH_4)_2SO_4$ | 16 |
| | L-Methionine | 0.08 |
| | L-Phenylalanine | 0.28 |
| | L-Tyrosine | 0.28 |
| | Mameno (total N) | 0.07 |
| B | Glucose | 40.0 |
| | $MgSO_4 7H_2O$ | 0.03 |
| C | $FeSO_4 7H_2O$ | 0.03 |
| D | $Na_2MoO_4 2H_2O$ | 0.00015 |
| | $H_3BO_3$ | 0.0025 |
| | $CoCl_2 6H_2O$ | 0.00007 |
| | $CuSO_4 5H_2O$ | 0.00025 |
| | $MnCl_2 4H_2O$ | 0.0016 |
| | $ZnSO_4 7 H_2O$ | 0.0003 |
| E | Thiamine HCl | 0.001 |
| F | $CaCO_3$ | 30.0 |
| G | Pyridoxine | 0.03 |

The pH of solution A is adjusted to 7.1 with $NH_4OH$.

Example 10

Production of L-Proline by *E. coli* Strain Having a Gene Coding for sRNA Deleted To test the effect of inactivation of a gene coding for sRNA on L-proline production, DNA fragments from the chromosome of the above-described mutant *E. coli* MG1655 having a gene coding for sRNA (target gene) deleted and marked with the Cm resistance gene can be transferred to the proline-producing *E. coli* strain 702ilvA by P1 transduction (Miller, J. H. Experiments in Molecular Genetics, Cold Spring Harbor Lab. Press, 1972, Plainview, N.Y.) to obtain strain 702ilvA-Δtarget gene. The strain 702ilvA has been deposited in the Russian National Collection of Industrial Microorganisms (VKPM) (Russia, 117545 Moscow, 1$^{st}$ Dorozhny proezd, 1) on Jul. 18, 2000 under accession number VKPM B-8012 and then converted to a deposit under the Budapest Treaty on May 18, 2001.

Both *E. coli* strains, 702ilvA and 702ilvA-Δtarget gene, can be grown for 18-24 hours at 37° C. on L-agar plates. Then, these strains can be cultivated under the same conditions as in Example 7.

Example 11

Production of L-Arginine by *E. coli* Strain Having a Gene Coding for sRNA Deleted To test the effect of inactivation of a gene coding for sRNA on L-arginine production, DNA fragments from the chromosome of the above-described mutant *E. coli* MG1655 having a gene coding for sRNA (target gene) deleted and marked with the Cm resistance gene can be transferred to the arginine-producing *E. coli* strain 382 by P1 transduction (Miller, J. H. Experiments in Molecular Genetics, Cold Spring Harbor Lab. Press, 1972, Plainview, N.Y.) to obtain strain 382-Δtarget gene. The strain 382 has been deposited in the Russian National Collection of Industrial Microorganisms (VKPM) (Russia, 117545 Moscow, 1$^{st}$ Dorozhny proezd, 1) on Apr. 10, 2000 under accession number VKPM B-7926 and then converted to a deposit under the Budapest Treaty on May 18, 2001. The strains 382-ΔgcvB::cat, 382-ΔrprA::cat, 382-ΔrygB-sraE::cat and 382-ΔsraH::cat were obtained in this manner.

Strains 382 and each of strains 382-ΔgcvB::cat, 382-ΔrprA::cat, 382-ΔrygB-sraE::cat or 382-ΔsraH::cat were separately cultivated with shaking at 37° C. for 18 hours in 3 ml of nutrient broth, and 0.3 ml of the obtained cultures were inoculated into 2 ml of a fermentation medium in 20×200-mm test tubes and cultivated at 32° C. for 48 hours on a rotary shaker.

After the cultivation, the amount of L-arginine which had accumulated in the medium was determined by paper chromatography using the following mobile phase: butanol:acetic acid:water=4:1:1 (v/v). A solution of ninhydrin (2%) in acetone was used as a visualizing reagent. A spot containing L-arginine was cut out, L-arginine was eluted with 0.5% water solution of $CdCl_2$, and the amount of L-arginine was estimated spectrophotometrically at 540 nm. The results of ten (for 382-ΔgcvB::cat and 382-ΔrprA::cat)/nine (for 382-ΔrygB-sraE::cat and 382-ΔsraH::cat) independent test tube fermentations are shown in Table 5. As follows from Table 5, 382-ΔgcvB::cat, 382-ΔrprA::cat, 382-ΔrygB-sraE::cat and 382-ΔsraH::cat produced a higher amount of L-arginine, as compared to 382.

TABLE 5

| Strain | $OD_{540}$ | Amount of L-arginine, g/l |
|---|---|---|
| 382 | 13.0 ± 2.2 | 9.7 ± 1.3 |
| 382-ΔgcvB | 12.9 ± 1.6 | 10.9 ± 0.8 |
| 382 | 13.8 ± 0.7 | 8.6 ± 0.4 |
| 382-ΔrprA | 13.4 ± 0.7 | 10.1 ± 0.8 |
| 382 | 14.2 ± 0.9 | 11.1 ± 0.7 |
| 382-ΔsraH | 15.0 ± 0.9 | 11.9 ± 0.7 |
| 382-ΔrygB-sraE | 14.0 ± 0.7 | 12.6 ± 0.4 |

The composition of the fermentation medium (g/l) was as follows:

| Glucose | 48.0 |
|---|---|
| $(NH4)_2SO_4$ | 35.0 |
| $KH_2PO_4$ | 2.0 |
| $MgSO_4 7H_2O$ | 1.0 |
| Thiamine HCl | 0.0002 |
| Yeast extract | 1.0 |
| L-isoleucine | 0.1 |
| $CaCO_3$ | 5.0 |

Glucose and magnesium sulfate were sterilized separately. $CaCO_3$ was dry-heat sterilized at 180° C. for 2 hours. The pH was adjusted to 7.0.

Example 12

Elimination of Cm Resistance Gene (Cat Gene) from the Chromosome of L-Amino Acid-Producing *E. coli* Strains The Cm resistance gene (cat gene) can be eliminated from the chromosome of the L-amino acid-producing strain using the int-xis system. For that purpose, an L-amino acid-producing strain having DNA fragments from the chromosome of the above-described *E. coli* strain MG1655 Δtarget gene::cat transferred by P1 transduction can be transformed with plasmid pMWts-Int/Xis. Transformant clones can be selected on the LB-medium containing 100 μg/ml of ampicillin. Plates can be incubated overnight at 30° C. Transformant clones can be cured from the cat gene by spreading the separate colonies at 37° C. (at that temperature repressor CIts is partially inactivated and transcription of the int/xis genes is derepressed) followed by selection of $Cm^S Ap^R$ variants. Elimination of the cat gene from the chromosome of the strain can be verified by PCR. Locus-specific primers P3 and P4 (see Table 1) can be used in PCR for the verification. Conditions for PCR verification can be as described above. The PCR product obtained in reaction with cells having the eliminated cat gene as a template should be much shorter (~0.3-0.5 kbp in length) then strain with cat gene.

Example 13

Production of L-Lysine Using an *Escherichia* Bacterium in which Expression of rygB-sraE Gene is Attenuated In order to evaluate the effect of rygB-sraE gene attenuation on L-lysine yield, a rygB-sraE-disrupted strain was constructed. The whole genome sequence of *Escherichia coli* K-12 strain has been disclosed (Science, 277, 1453-1474 (1997)). The nucleotide sequence of rygB-sraE gene is also disclosed, and the strain can be constructed based on the sequence.

(1) Disruption of the rygB-sraE Gene

The rygB-sraE gene was disrupted according to the method called "Red-driven integration" that was developed by Datsenko and Wanner (Proc. Natl. Acad. Sci. USA, 2000, vol. 97, No. 12, p 6640-6645). "Red-driven integration" makes it possible to construct a gene-disrupted strain in one step by employing a PCR product obtained by using as primers synthetic oligonucleotides designed to have a part of the targeted gene on the 5'-ends and a part of an antibiotic-resistance gene on the 3'-ends. According to this method, primers which are complementary to a region proximal to the rygB-sraE gene and to a region proximal to a gene conferring antibiotic resistance to a template plasmid, respectively, were designed. PCR was performed using the oligonucleotides of SEQ ID NOS: 117 and 118 and the plasmid pMW118-att-cat as a template.

The obtained PCR product was purified by using an agarose gel, and used to transform the *E. coli* WC196LC strain that carries a plasmid pKD46 that has temperature-sensitive replication ability. pKD46 contains a DNA fragment of 2,154 nucleotides derived from λ phage which contains the Red recombinase-encoding genes (γ, β, and exo genes) of the λ Red homologous recombination system, which is controlled by an arabinose-inducible ParaB promoter (GenBank/EMBL Accession No. J02459, nucleotide numbers 31088 to 33241). pKD46 is necessary to integrate the PCR product into the chromosome of the WC196LC strain. The WC196LC strain (WO2006/038695) is an L-lysine-producing strain obtained by disrupting lysine decarboxylase genes (cadA and ldcC) in the WC196 strain (FERM BP-5252).

Competent cells for electroporation were prepared as follows. *E. coli* WC196LC/pKD46 strain was cultured overnight at 30° C. in LB medium that contained 100 mg/L of ampicillin, and then was diluted to 100-fold with 5 ml of SOB medium (Molecular Cloning Laboratory Manual 2nd Edition, Sambrook, J. et al., Cold Spring Harbor Laboratory Press (1989)) that contained ampicillin and L-arabinose (1 mM). The diluted cells were grown at 30° C. with aeration until OD600 became approximately 0.6, and then concentrated to 100-fold and washed with ice-cold 10% glycerol solution three times, which were then used for electroporation. Electroporation was performed using 40 μL of the competent cells and about 100 ng of the PCR product. After electroporation, the cells were added to 1 mL of SOC medium (Molecular Cloning Laboratory Manual 2nd Edition, Sambrook, J. et al., Cold Spring Harbor Laboratory Press (1989)) and cultured at 37° C. for 1 hour, and then cultured overnight at 37° C. on L-agar medium containing chloramphenicol to select a chloramphenicol-resistant recombinant strain. Then, in order to cure the pKD46 plasmid, the strain was subjected to passage culture twice at 42° C. on L-agar medium containing chloramphenicol, and the ampicillin-resistance of the obtained strains was tested to select an ampicillin-sensitive strain due to curing of the pKD46 plasmid.

The disruption of the rygB-sraE gene in the obtained strain was confirmed by PCR based on the presence of the chloramphenicol-resistant gene. The obtained rygB-sraE-disrupted strain was named WC196LCΔrygB-sraE.

(2) The Effect of rygB-sra Gene Disruption on the *E. coli* L-Lysine-Producing Strain According to a conventional method, the WC196LC strain and WC196LCΔrygB-sraE strain were transformed with the plasmid pCABD2 (WO01/53459), which is a plasmid for L-lysine production containing the dapA gene, dapB gene, lysC gene and ddh gene, to prepare a WC196LC/pCABD2 strain and WC196LCΔrygB-sraE/pCABD2 strain.

The WC196LC/pCABD2 strain and WC196LCΔrygB-sraE/pCABD2 strain were cultured at 37° C. in L medium contains 20 mg/L of streptomycin until OD600 became approximately 0.6, and then added to an equal volume of 40% glycerol solution and mixed. Then, the mixture was dispensed in an appropriate volume and stocked at −80° C., which was used as a glycerol stock.

The glycerol stocks of these strains were thawed, and 100 μl of each of the strains was spread uniformly over an L plate containing 20 mg/L of streptomycin and cultured at 37° C. for 24 hours. About one eighth of the cells of each strain on the plate was inoculated into 20 mL of the fermentation medium that has the composition shown below and further contains 20 mg/L of streptomycin in 500 mL-volume Sakaguchi flask, and cultured at 37° C. for 24 hours with reciprocal shaker. The amount of L-lysine that accumulated in the medium was analyzed by using Biotech Analyze AS210 (Sakura Seiki).

Table 6 shows OD600 and L-lysine accumulation after 24 hour culture. It was revealed from this result that L-lysine accumulation was improved by disrupting the rygB-sraE gene.

L-Lysine Production Medium:

| | |
|---|---|
| Glucose | 40 g/L |
| $(NH_4)_2SO_4$ | 24 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 5H_2O$ | 0.01 g/L |
| Yeast extract | 2.0 g/L |
| Calcium carbonate (Official grade) | 30 g/L |

The medium was adjusted to pH 7.0 with potassium hydroxide and sterilized by steam at 115° C. for 10 minutes.

Glucose and $MgSO_4 \cdot 7H_2O$ were separately sterilized.

Calcium carbonate (Official grade) was separately sterilized by heating at 180° C.

TABLE 6

| Strain | OD600 | L-lysine accumulation (g/L) |
|---|---|---|
| WC196LC/pCABD2 | 14.1 | 10.5 |
| WC196LCΔrygB-sraE/pCABD2 | 18.1 | 12.8 |

*The amount of L-lysine accumulation was shown by the amount of hydrochloride salt of L-lysine.

Example 14

Production of L-Lysine Using an *Escherichia* Bacterium in which Expression of gcvB Gene is Attenuated In order to evaluate the effect of gcvB gene attenuation on L-lysine yield, a gcvB-disrupted strain was constructed. The whole genome sequence of *Escherichia coli* K-12 strain has been disclosed (Science, 277, 1453-1474 (1997)). The nucleotide sequence of gcv gene is also disclosed, and the strain can be constructed based on the sequence.

(1) Disruption of the gcvB Gene

The gcvB gene was disrupted according to the method called "Red-driven integration" that was developed by Datsenko and Wanner (Proc. Natl. Acad. Sci. USA, 2000, vol. 97, No. 12, p 6640-6645). According to this method, primers which are complementary to a region proximal to the gcvB gene and to a region proximal to a gene conferring antibiotic resistance to a template plasmid, respectively, were designed. PCR was performed using the oligonucleotides of SEQ ID NOS: 119 and 120 and the plasmid pMW118-att-cat as a template.

The obtained PCR product was purified by using an agarose gel, and used to transform the *E. coli* WC196LC strain that carries a plasmid pKD46 that has temperature-sensitive replication ability.

Competent cells for electroporation were prepared as follows. *E. coli* WC196LC/pKD46 strain was cultured overnight at 30° C. in LB medium that contained 100 mg/L of ampicillin, and then was diluted to 100-fold with 5 ml of SOB medium that contained ampicillin and L-arabinose (1 mM). The diluted cells were grown at 30° C. with aeration until OD600 became approximately 0.6, and then concentrated to 100-fold and washed with ice-cold 10% glycerol solution three times, which were used for electroporation. Electroporation was performed using 40 μL of the competent cells and about 100 ng of the PCR product. After electroporation, the cells were added to 1 mL of SOC medium and cultured at 37° C. for 1 hour, and then cultured overnight at 37° C. on L-agar medium containing chloramphenicol to select a chloramphenicol-resistant recombinant strain. Then, in order to cure the pKD46 plasmid, the strain was subjected to passage culture twice at 42° C. on L-agar medium containing chloramphenicol, and the ampicillin-resistance of the obtained strains was tested to select an ampicillin-sensitive strain due to curing of the pKD46 plasmid.

The disruption of the gcvB gene in the obtained strain was confirmed by PCR based on the presence of the chloramphenicol-resistant gene. The obtained gcvB-disrupted strain was named WC196LCΔgcvB.

(2) The Effect of gcvB Gene Disruption on an *E. coli* L-Lysine-Producing Strain According to a conventional method, the WC196LC strain and WC196LCΔgcvB strain were transformed with the plasmid pCABD2 to prepare a WC196LC/pCABD2 strain and WC196LCΔgcvB/pCABD2 strain.

The WC196LC/pCABD2 strain and WC196LCΔgcvB/pCABD2 strain were cultured at 37° C. in L medium containing 20 mg/L of streptomycin until OD600 became approximately 0.6, and then added to an equal volume of 40% glycerol solution and mixed. Then, the mixture was dispensed in an appropriate volume and stocked at −80° C., which was used as a glycerol stock.

The glycerol stocks of these strains were thawed, and 100 μl of each of the strains was spread uniformly over an L plate containing 20 mg/L of streptomycin and cultured at 37° C. for 24 hours. About one eighth of the cells of each strain on the plate was inoculated into 20 mL of the fermentation medium that has a composition shown below and further contains 20 mg/L of streptomycin in 500 mL-volume Sakaguchi flask, and cultured at 37° C. for 24 hours with reciprocal shaker. The amount of L-lysine that accumulated in the medium was analyzed by using Biotech Analyze AS210 (Sakura Seiki).

Table 7 shows OD600 and L-lysine accumulation after 24 hour culture. It was revealed from this result that L-lysine accumulation was improved by disrupting the gcvB gene.

TABLE 7

| Strain | OD600 | L-lysine accumulation (g/L) |
|---|---|---|
| WC196LC/pCABD2 | 14.1 | 10.5 |
| WC196LCΔgcvB/pCABD2 | 18.6 | 13.4 |

*The amount of L-lysine accumulation was shown by the amount of hydrochloride salt of L-lysine.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

The invention claimed is:

1. A method for producing an L-amino acid comprising: cultivating an *Escherichia coli* in a medium, and collecting said L-amino acid from the medium, wherein said *Escherichia coli* has been modified to attenuate expression of sraD gene, wherein said L-amino acid is selected from the group consisting of L-threonine, L-lysine, and combinations thereof.

2. The method according to claim 1, wherein said sraD gene comprises a nucleotide sequence that hybridizes with a complement of the nucleotide sequence of SEQ ID NO: 98 under stringent conditions comprising washing at 0.1×SSC, 0.1% SDS at 60° C.

3. The method according to claim 1, wherein said sraD gene comprises the nucleotide sequence of SEQ ID NO: 98.

* * * * *

SEQUENCE LISTING

```
<160> NUMBER OF SEQ ID NOS: 120

<210> SEQ ID NO 1
<211> LENGTH: 386
<212> TYPE: DNA
<213> ORGANISM: Escherichia coli

<400> SEQUENCE: 1
aactttaagc tgaaaatggc gctgtaaaag gcgccatttt catattgtag acaacgtagg      60
ctttgttcat gccggatgcg gcgtgaacgc cttatccggc atgaaaaccc ttcaaatcca     120
atagattgca gtgaacgtgt aggcctgata agcgtagcgc atcaggcaat gttgcgtttg     180
tcatcagttt caaatggcgc tgtaaaaggc gtcattttca tattgtagac aacgtaggct     240
ttgttcatgc cggatgcggc gtgaacgcct tatccggcat gaaaaccctt caaatccaat     300
agattgcagt gaacgtgtag gcctgataag cgtagcgcat caggcaatgt tgcgtttgtc     360
atcagttcta aatggcgctt tataaa                                          386

<210> SEQ ID NO 2
<211> LENGTH: 78
<212> TYPE: DNA
<213> ORGANISM: Escherichia coli

<400> SEQUENCE: 2
gggaaacttt attgctgatg ccacccgccg cgaaattgaa ataaaaaacc cgatgcgcag      60
atcatcgggt tcatttca                                                    78

<210> SEQ ID NO 3
<211> LENGTH: 87
<212> TYPE: DNA
<213> ORGANISM: Escherichia coli

<400> SEQUENCE: 3
```

```
aacacatcag atttcctggt gtaacgaatt ttttaagtgc ttcttgctta agcaagtttc    60
atcccgaccc cctcagggtc gggattt                                        87
```

<210> SEQ ID NO 4
<211> LENGTH: 205
<212> TYPE: DNA
<213> ORGANISM: Escherichia coli

<400> SEQUENCE: 4

```
acttcctgag ccggaacgaa aagtttttatc ggaatgcgtg ttctggtgaa cttttggctt   60
acggttgtga tgttgtgttg ttgtgtttgc aattggtctg cgattcagac catggtagca   120
aagctacctt ttttcacttc ctgtacattt accctgtctg tccatagtga ttaatgtagc   180
accgcctaat tgcggtgctt ttttt                                         205
```

<210> SEQ ID NO 5
<211> LENGTH: 108
<212> TYPE: DNA
<213> ORGANISM: Escherichia coli

<400> SEQUENCE: 5

```
gttatatgcc tttattgtca cagatttttat tttctgttgg gccattgcat tgccactgat   60
tttccaacat ataaaaagac aagcccgaac agtcgtccgg gcttttttt                108
```

<210> SEQ ID NO 6
<211> LENGTH: 105
<212> TYPE: DNA
<213> ORGANISM: Escherichia coli

<400> SEQUENCE: 6

```
acggttataa atcaacatat tgatttataa gcatggaaat cccctgagtg aaacaacgaa    60
ttgctgtgtg tagtctttgc ccatctccca cgatgggctt ttttt                   105
```

<210> SEQ ID NO 7
<211> LENGTH: 79
<212> TYPE: DNA
<213> ORGANISM: Escherichia coli

<400> SEQUENCE: 7

```
actgcttttc tttgatgtcc ccattttgtg gagcccatca accccgccat ttcggttcaa    60
ggttgatggg ttttttgtt                                                 79
```

<210> SEQ ID NO 8
<211> LENGTH: 86
<212> TYPE: DNA
<213> ORGANISM: Escherichia coli

<400> SEQUENCE: 8

```
tcgctgaaaa acataaccca taaaatgcta gctgtaccag gaaccacctc cttagcctgt    60
gtaatctccc ttacacgggc ttattt                                         86
```

<210> SEQ ID NO 9
<211> LENGTH: 76
<212> TYPE: DNA
<213> ORGANISM: Escherichia coli

<400> SEQUENCE: 9

```
cccagaggta ttgataggtg aagtcaactt cgggttgagc acatgaatta caccagcctg    60
cgcagatgcg caggtt                                                    76
```

<210> SEQ ID NO 10
<211> LENGTH: 57
<212> TYPE: DNA
<213> ORGANISM: Escherichia coli

<400> SEQUENCE: 10
cattcaacgc cgagaataga ggaaaaatta aagggagat aaaatccccc cttttg        57

<210> SEQ ID NO 11
<211> LENGTH: 169
<212> TYPE: DNA
<213> ORGANISM: Escherichia coli

<400> SEQUENCE: 11
taggcatatt ttttccatc agatatagcg tattgatgat agccatttta aactatgcgc    60
ttcgttttgc aggttgatgt tgttatcag cactgaacga aaataaagca gtaacccgca   120
atgtgtgcga attattggca aaaggcaacc acaggctgcc ttttctttt               169

<210> SEQ ID NO 12
<211> LENGTH: 88
<212> TYPE: DNA
<213> ORGANISM: Escherichia coli

<400> SEQUENCE: 12
cccagaggta ttgattggtg agattattcg gtacgctctt cgtaccctgt ctcttgcacc    60
aacctgcgcg gatgcgcagg ttttttt                                       88

<210> SEQ ID NO 13
<211> LENGTH: 108
<212> TYPE: DNA
<213> ORGANISM: Escherichia coli

<400> SEQUENCE: 13
gtgcggcctg aaaaacagtg ctgtgccctt gtaactcatc ataataattt acggcgcagc    60
caagatttcc ctggtgttgg cgcagtattc gcgcaccccg gtctagcc                108

<210> SEQ ID NO 14
<211> LENGTH: 92
<212> TYPE: DNA
<213> ORGANISM: Escherichia coli

<400> SEQUENCE: 14
ataacgtgat gggaagcgcc tcgcttcccg tgtatgattg aacccgcatg gctcccgaaa    60
cattgaggga agcgttgagg gttcattttt at                                  92

<210> SEQ ID NO 15
<211> LENGTH: 24
<212> TYPE: DNA
<213> ORGANISM: Artificial sequence
<220> FEATURE:
<223> OTHER INFORMATION: 3' region of primer P1

<400> SEQUENCE: 15
cgctcaagtt agtataaaaa agct                                           24

<210> SEQ ID NO 16
<211> LENGTH: 24
<212> TYPE: DNA
<213> ORGANISM: Artificial sequence
<220> FEATURE:
<223> OTHER INFORMATION: 3' region of primer P2

```
<400> SEQUENCE: 16
tgaagcctgc ttttttatac taag                                            24

<210> SEQ ID NO 17
<211> LENGTH: 60
<212> TYPE: DNA
<213> ORGANISM: Artificial sequence
<220> FEATURE:
<223> OTHER INFORMATION: primer

<400> SEQUENCE: 17
ttacgccgtc tggttacgca ataaaaaaat ggcacttgaa gcctgctttt ttatactaag     60

<210> SEQ ID NO 18
<211> LENGTH: 59
<212> TYPE: DNA
<213> ORGANISM: Artificial sequence
<220> FEATURE:
<223> OTHER INFORMATION: primer

<400> SEQUENCE: 18
ttcatgccgg atgcggcgtg aacgccttat ccggccgctc aagttagtat aaaaaagct     59

<210> SEQ ID NO 19
<211> LENGTH: 18
<212> TYPE: DNA
<213> ORGANISM: Artificial sequence
<220> FEATURE:
<223> OTHER INFORMATION: primer

<400> SEQUENCE: 19
aagggaaggt aagtcgtc                                                   18

<210> SEQ ID NO 20
<211> LENGTH: 18
<212> TYPE: DNA
<213> ORGANISM: Artificial sequence
<220> FEATURE:
<223> OTHER INFORMATION: primer

<400> SEQUENCE: 20
agcaatggaa attgctcc                                                   18

<210> SEQ ID NO 21
<211> LENGTH: 60
<212> TYPE: DNA
<213> ORGANISM: Artificial sequence
<220> FEATURE:
<223> OTHER INFORMATION: primer

<400> SEQUENCE: 21
gtcagaagtg gcgtaattct cccgatttcc tcaatttgaa gcctgctttt ttatactaag     60

<210> SEQ ID NO 22
<211> LENGTH: 59
<212> TYPE: DNA
<213> ORGANISM: Artificial sequence
<220> FEATURE:
<223> OTHER INFORMATION: primer

<400> SEQUENCE: 22
tgaaaacaag ttgatctcgt tatcggcaag gagggcgctc aagttagtat aaaaaagct     59

<210> SEQ ID NO 23
<211> LENGTH: 18
```

```
<212> TYPE: DNA
<213> ORGANISM: Artificial sequence
<220> FEATURE:
<223> OTHER INFORMATION: primer

<400> SEQUENCE: 23
agcaccatta ccaacagc                                                     18

<210> SEQ ID NO 24
<211> LENGTH: 18
<212> TYPE: DNA
<213> ORGANISM: Artificial sequence
<220> FEATURE:
<223> OTHER INFORMATION: primer

<400> SEQUENCE: 24
tgattctggt gaacatcg                                                     18

<210> SEQ ID NO 25
<211> LENGTH: 60
<212> TYPE: DNA
<213> ORGANISM: Artificial sequence
<220> FEATURE:
<223> OTHER INFORMATION: primer

<400> SEQUENCE: 25
acttcagcgt ctctgaagtg aatcgttgaa tgcacatgaa gcctgctttt ttatactaag       60

<210> SEQ ID NO 26
<211> LENGTH: 59
<212> TYPE: DNA
<213> ORGANISM: Artificial sequence
<220> FEATURE:
<223> OTHER INFORMATION: primer

<400> SEQUENCE: 26
aattgcggat aaggtgatga acacatcaga tttcccgctc aagttagtat aaaaaagct        59

<210> SEQ ID NO 27
<211> LENGTH: 21
<212> TYPE: DNA
<213> ORGANISM: Artificial sequence
<220> FEATURE:
<223> OTHER INFORMATION: primer

<400> SEQUENCE: 27
agtactcctc ttaccaggat g                                                 21

<210> SEQ ID NO 28
<211> LENGTH: 18
<212> TYPE: DNA
<213> ORGANISM: Artificial sequence
<220> FEATURE:
<223> OTHER INFORMATION: primer

<400> SEQUENCE: 28
acacgttagc gtcgatgg                                                     18

<210> SEQ ID NO 29
<211> LENGTH: 60
<212> TYPE: DNA
<213> ORGANISM: Artificial sequence
<220> FEATURE:
<223> OTHER INFORMATION: primer

<400> SEQUENCE: 29
ggtcgaactg gatcagtaat tcgcgatcgc aaggtatgaa gcctgctttt ttatactaag       60
```

<210> SEQ ID NO 30
<211> LENGTH: 59
<212> TYPE: DNA
<213> ORGANISM: Artificial sequence
<220> FEATURE:
<223> OTHER INFORMATION: primer

<400> SEQUENCE: 30
ttgagcttct accagcaaat acctatagtg gcggccgctc aagttagtat aaaaaagct      59

<210> SEQ ID NO 31
<211> LENGTH: 20
<212> TYPE: DNA
<213> ORGANISM: Artificial sequence
<220> FEATURE:
<223> OTHER INFORMATION: primer

<400> SEQUENCE: 31
tcctcaagag acttgatttg      20

<210> SEQ ID NO 32
<211> LENGTH: 18
<212> TYPE: DNA
<213> ORGANISM: Artificial sequence
<220> FEATURE:
<223> OTHER INFORMATION: primer

<400> SEQUENCE: 32
agcagatcaa ccgtactg      18

<210> SEQ ID NO 33
<211> LENGTH: 60
<212> TYPE: DNA
<213> ORGANISM: Artificial sequence
<220> FEATURE:
<223> OTHER INFORMATION: primer

<400> SEQUENCE: 33
gattaaatgc tctggataag gattatccaa ttctaatgaa gcctgctttt ttatactaag      60

<210> SEQ ID NO 34
<211> LENGTH: 59
<212> TYPE: DNA
<213> ORGANISM: Artificial sequence
<220> FEATURE:
<223> OTHER INFORMATION: primer

<400> SEQUENCE: 34
tatactttta atttgctata cgttattctg cgcggcgctc aagttagtat aaaaaagct      59

<210> SEQ ID NO 35
<211> LENGTH: 19
<212> TYPE: DNA
<213> ORGANISM: Artificial sequence
<220> FEATURE:
<223> OTHER INFORMATION: primer

<400> SEQUENCE: 35
aagtctggtg aatgtatcg      19

<210> SEQ ID NO 36
<211> LENGTH: 18
<212> TYPE: DNA
<213> ORGANISM: Artificial sequence
<220> FEATURE:
<223> OTHER INFORMATION: primer

```
<400> SEQUENCE: 36
atggaaagat gctgcagc                                                    18

<210> SEQ ID NO 37
<211> LENGTH: 60
<212> TYPE: DNA
<213> ORGANISM: Artificial sequence
<220> FEATURE:
<223> OTHER INFORMATION: primer

<400> SEQUENCE: 37
agtgaggggc gaggtagcga agcggaaaaa tgttaatgaa gcctgctttt ttatactaag      60

<210> SEQ ID NO 38
<211> LENGTH: 59
<212> TYPE: DNA
<213> ORGANISM: Artificial sequence
<220> FEATURE:
<223> OTHER INFORMATION: primer

<400> SEQUENCE: 38
atcgacgcaa aaagtccgta tgcctactat tagctcgctc aagttagtat aaaaaagct       59

<210> SEQ ID NO 39
<211> LENGTH: 18
<212> TYPE: DNA
<213> ORGANISM: Artificial sequence
<220> FEATURE:
<223> OTHER INFORMATION: primer

<400> SEQUENCE: 39
ttcagctggt agtacctg                                                    18

<210> SEQ ID NO 40
<211> LENGTH: 18
<212> TYPE: DNA
<213> ORGANISM: Artificial sequence
<220> FEATURE:
<223> OTHER INFORMATION: primer

<400> SEQUENCE: 40
tcataagcgt tcatcgtg                                                    18

<210> SEQ ID NO 41
<211> LENGTH: 60
<212> TYPE: DNA
<213> ORGANISM: Artificial sequence
<220> FEATURE:
<223> OTHER INFORMATION: primer

<400> SEQUENCE: 41 aactttccg cagggcatca gtcttaatta gtgccatgaa gcctgctttt ttatactaag       60

<210> SEQ ID NO 42
<211> LENGTH: 59
<212> TYPE: DNA
<213> ORGANISM: Artificial sequence
<220> FEATURE:
<223> OTHER INFORMATION: primer

<400> SEQUENCE: 42
ttgagagggt tgcagggtag tagataagtt ttagacgctc aagttagtat aaaaaagct       59

<210> SEQ ID NO 43
<211> LENGTH: 18
```

```
<212> TYPE: DNA
<213> ORGANISM: Artificial sequence
<220> FEATURE:
<223> OTHER INFORMATION: primer

<400> SEQUENCE: 43
tggagctgat gtaccagc                                                      18

<210> SEQ ID NO 44
<211> LENGTH: 20
<212> TYPE: DNA
<213> ORGANISM: Artificial sequence
<220> FEATURE:
<223> OTHER INFORMATION: primer

<400> SEQUENCE: 44
atcatcagtg atacagctcg                                                    20

<210> SEQ ID NO 45
<211> LENGTH: 60
<212> TYPE: DNA
<213> ORGANISM: Artificial sequence
<220> FEATURE:
<223> OTHER INFORMATION: primer

<400> SEQUENCE: 45
aataaatcct tttatttcat tgtattacgc gtaaaatgaa gcctgctttt ttatactaag        60

<210> SEQ ID NO 46
<211> LENGTH: 59
<212> TYPE: DNA
<213> ORGANISM: Artificial sequence
<220> FEATURE:
<223> OTHER INFORMATION: primer

<400> SEQUENCE: 46
acatacagct gcatttatta aggttatcat ccgttcgctc aagttagtat aaaaaagct         59

<210> SEQ ID NO 47
<211> LENGTH: 19
<212> TYPE: DNA
<213> ORGANISM: Artificial sequence
<220> FEATURE:
<223> OTHER INFORMATION: primer

<400> SEQUENCE: 47
aggcgatggt tatactgtg                                                     19

<210> SEQ ID NO 48
<211> LENGTH: 18
<212> TYPE: DNA
<213> ORGANISM: Artificial sequence
<220> FEATURE:
<223> OTHER INFORMATION: primer

<400> SEQUENCE: 48
ttatgagtcg gtacagcg                                                      18

<210> SEQ ID NO 49
<211> LENGTH: 60
<212> TYPE: DNA
<213> ORGANISM: Artificial sequence
<220> FEATURE:
<223> OTHER INFORMATION: primer

<400> SEQUENCE: 49
ggtggcgttt ggcttcaggt tgctaaagtg gtgatctgaa gcctgctttt ttatactaag        60
```

<210> SEQ ID NO 50
<211> LENGTH: 59
<212> TYPE: DNA
<213> ORGANISM: Artificial sequence
<220> FEATURE:
<223> OTHER INFORMATION: primer

<400> SEQUENCE: 50
gagataaaga acgcgagcga cagtaaatta ggtgccgctc aagttagtat aaaaaagct    59

<210> SEQ ID NO 51
<211> LENGTH: 20
<212> TYPE: DNA
<213> ORGANISM: Artificial sequence
<220> FEATURE:
<223> OTHER INFORMATION: primer

<400> SEQUENCE: 51
aagctaaaaa gcattccaac                                                20

<210> SEQ ID NO 52
<211> LENGTH: 18
<212> TYPE: DNA
<213> ORGANISM: Artificial sequence
<220> FEATURE:
<223> OTHER INFORMATION: primer

<400> SEQUENCE: 52
tttcatcgtg ggaatgtg                                                  18

<210> SEQ ID NO 53
<211> LENGTH: 60
<212> TYPE: DNA
<213> ORGANISM: Artificial sequence
<220> FEATURE:
<223> OTHER INFORMATION: primer

<400> SEQUENCE: 53
taacatgtac gtcagtatat ggggatgttt cccccatgaa gcctgctttt ttatactaag   60

<210> SEQ ID NO 54
<211> LENGTH: 59
<212> TYPE: DNA
<213> ORGANISM: Artificial sequence
<220> FEATURE:
<223> OTHER INFORMATION: primer

<400> SEQUENCE: 54
tgaataatta accattccca tacaattagt taacccgctc aagttagtat aaaaaagct    59

<210> SEQ ID NO 55
<211> LENGTH: 18
<212> TYPE: DNA
<213> ORGANISM: Artificial sequence
<220> FEATURE:
<223> OTHER INFORMATION: primer

<400> SEQUENCE: 55
atctgccgtc catggaag                                                  18

<210> SEQ ID NO 56
<211> LENGTH: 18
<212> TYPE: DNA
<213> ORGANISM: Artificial sequence
<220> FEATURE:
<223> OTHER INFORMATION: primer

```
<400> SEQUENCE: 56
tcagatgaca cgactgtg                                              18

<210> SEQ ID NO 57
<211> LENGTH: 60
<212> TYPE: DNA
<213> ORGANISM: Artificial sequence
<220> FEATURE:
<223> OTHER INFORMATION: primer

<400> SEQUENCE: 57
gcatattaac tttgtaacgt catagagtca aagaaatgaa gcctgctttt ttatactaag  60

<210> SEQ ID NO 58
<211> LENGTH: 59
<212> TYPE: DNA
<213> ORGANISM: Artificial sequence
<220> FEATURE:
<223> OTHER INFORMATION: primer

<400> SEQUENCE: 58
ttttccatca gatatagcgt attgatgata gccatcgctc aagttagtat aaaaaagct   59

<210> SEQ ID NO 59
<211> LENGTH: 19
<212> TYPE: DNA
<213> ORGANISM: Artificial sequence
<220> FEATURE:
<223> OTHER INFORMATION: primer

<400> SEQUENCE: 59
tgcagttttt ccagaagag                                             19

<210> SEQ ID NO 60
<211> LENGTH: 18
<212> TYPE: DNA
<213> ORGANISM: Artificial sequence
<220> FEATURE:
<223> OTHER INFORMATION: primer

<400> SEQUENCE: 60
acatcactgt ccacactg                                              18

<210> SEQ ID NO 61
<211> LENGTH: 60
<212> TYPE: DNA
<213> ORGANISM: Artificial sequence
<220> FEATURE:
<223> OTHER INFORMATION: primer

<400> SEQUENCE: 61
agcgtgggtg gcaaaagcca ctaaaaaatg accccgtgaa gcctgctttt ttatactaag  60

<210> SEQ ID NO 62
<211> LENGTH: 59
<212> TYPE: DNA
<213> ORGANISM: Artificial sequence
<220> FEATURE:
<223> OTHER INFORMATION: primer

<400> SEQUENCE: 62
tgtaacaaat catttaagtt ttgctatctt aactgcgctc aagttagtat aaaaaagct   59

<210> SEQ ID NO 63
<211> LENGTH: 20
```

```
<212> TYPE: DNA
<213> ORGANISM: Artificial sequence
<220> FEATURE:
<223> OTHER INFORMATION: primer

<400> SEQUENCE: 63
tagctaacaa cgtcaacacc                                                    20

<210> SEQ ID NO 64
<211> LENGTH: 18
<212> TYPE: DNA
<213> ORGANISM: Artificial sequence
<220> FEATURE:
<223> OTHER INFORMATION: primer

<400> SEQUENCE: 64
tcagcaaatt cagtctcc                                                      18

<210> SEQ ID NO 65
<211> LENGTH: 60
<212> TYPE: DNA
<213> ORGANISM: Artificial sequence
<220> FEATURE:
<223> OTHER INFORMATION: primer

<400> SEQUENCE: 65
gcgcgtcgaa ttgacgttca gcaggttgaa aaataatgaa gcctgctttt ttatactaag        60

<210> SEQ ID NO 66
<211> LENGTH: 59
<212> TYPE: DNA
<213> ORGANISM: Artificial sequence
<220> FEATURE:
<223> OTHER INFORMATION: primer

<400> SEQUENCE: 66
gaatgttttt tgccacgttt attctctttc tgaatcgctc aagttagtat aaaaaagct         59

<210> SEQ ID NO 67
<211> LENGTH: 18
<212> TYPE: DNA
<213> ORGANISM: Artificial sequence
<220> FEATURE:
<223> OTHER INFORMATION: primer

<400> SEQUENCE: 67
tcagtgtgcc ttcaatgc                                                      18

<210> SEQ ID NO 68
<211> LENGTH: 18
<212> TYPE: DNA
<213> ORGANISM: Artificial sequence
<220> FEATURE:
<223> OTHER INFORMATION: primer

<400> SEQUENCE: 68
tgatcgacca gctggaag                                                      18

<210> SEQ ID NO 69
<211> LENGTH: 125
<212> TYPE: DNA
<213> ORGANISM: Escherichia coli

<400> SEQUENCE: 69
atgtctgtgg cgaaattgac taccttcgtt tttttgatta agaatgattt tattatcgta        60
agtaaaatta catgaatatt taaaaggaa acgacatga aaccgaagca cagaatcaac         120
``` attct 125

<210> SEQ ID NO 70
<211> LENGTH: 73
<212> TYPE: DNA
<213> ORGANISM: Escherichia coli

<400> SEQUENCE: 70
tcacccggga ctcgccaggg gacagccaac aggcattggg tgcaatcacc ttagcgttca 60
ggtacatgcg gaa 73

<210> SEQ ID NO 71
<211> LENGTH: 79
<212> TYPE: DNA
<213> ORGANISM: Escherichia coli

<400> SEQUENCE: 71
gccacgtgag cacaagataa gagaacgaaa aatcagcagc ctatgcagcg acaaatattg 60
atagcctgaa tcagtattg 79

<210> SEQ ID NO 72
<211> LENGTH: 75
<212> TYPE: DNA
<213> ORGANISM: Escherichia coli

<400> SEQUENCE: 72
ctgttccagt gcccgatccg atccctcgcc cgcaacccat gcctgaccca ccacccgatg 60
aagaaccgat taaat 75

<210> SEQ ID NO 73
<211> LENGTH: 87
<212> TYPE: DNA
<213> ORGANISM: Escherichia coli

<400> SEQUENCE: 73
ggccggtgtc gataatacgc taaataaaca ataattactc tcttttgctt gacaaaaga 60 gagttactgg tgagtattgt tttgctg 87

<210> SEQ ID NO 74
<211> LENGTH: 113
<212> TYPE: DNA
<213> ORGANISM: Escherichia coli

<400> SEQUENCE: 74
tgtgcctaaa atgtcggatg cgacgctggc gcgtcttatc cgacctacgg ggacgcatgt 60
gtaggccgga taaggcgttt acgccgcatc cggcaatggt gtccaaatgc aac 113

<210> SEQ ID NO 75
<211> LENGTH: 222
<212> TYPE: DNA
<213> ORGANISM: Escherichia coli

<400> SEQUENCE: 75
tataggcgtt atactttaca gcaacagtac gccgctaacg caattgctac ctctggcata 60
acaagtatat cgggtaaggg tttctgttcc gcacacgcag acgcagagta tcgttaagat 120
gtccatattg ttgttttagg cccgctagta atgcgctacg ggtatttaat attgttaaac 180
cctgataatc gctccggtta tttccgggat aaatgtacta cc 222

```
<210> SEQ ID NO 76
<211> LENGTH: 360
<212> TYPE: DNA
<213> ORGANISM: Escherichia coli

<400> SEQUENCE: 76
gagtcagaca acgaagtgaa catcaggatg atgacacttc tgcaggacac accaggatgg      60
tgtttcaggg aaaggcttct ggatgaagcg aagaggatga cgcaggacgc gttaaaggac     120
acctccagga tggagaatga gaaccggtca ggatgattcg gtgggtcagg aaggccaggg     180
acacttcagg atgaagtatc acatcggggt ggtgtgagca ggaagcaata gttcaggatg     240
aacgattggc cgcaaggcca gaggaaaagt tgtcaaggat gagcagggag caacaaaagt     300
agctggaatg ctgcgaaacg aaccgggagc gctgtgaata cagtgctccc ttttttt att     360

<210> SEQ ID NO 77
<211> LENGTH: 53
<212> TYPE: DNA
<213> ORGANISM: Escherichia coli

<400> SEQUENCE: 77
tttctggtga cgtttggcgg tatcagtttt actccgtgac tgctctgccg ccc            53

<210> SEQ ID NO 78
<211> LENGTH: 114
<212> TYPE: DNA
<213> ORGANISM: Escherichia coli

<400> SEQUENCE: 78
gggggctctg ttggttctcc cgcaacgcta ctctgtttac caggtcaggt ccggaaggaa      60
gcagccaagg cagatgacgc gtgtgccggg atgtagctgg cagggccccc accc           114

<210> SEQ ID NO 79
<211> LENGTH: 105
<212> TYPE: DNA
<213> ORGANISM: Escherichia coli

<400> SEQUENCE: 79
actgagagca caaagtttcc cgtgccaaca gggagtgtta taacggttta ttagtctgga      60
gacggcagac tatcctcttc ccggtcccct atgccgggtt ttttt               105

<210> SEQ ID NO 80
<211> LENGTH: 160
<212> TYPE: DNA
<213> ORGANISM: Escherichia coli

<400> SEQUENCE: 80
gacaataaca cctgtataac aaatggtcgg agtgccgcga tgaaactgcg caaaatcctg      60
aaaagtatgt tcaataacta ttgcaagacg ttcaaagacg taccgccagg caatatgttc     120
cgataacaaa aaacctgctc cggcaggttt ttttgtgtcc                           160

<210> SEQ ID NO 81
<211> LENGTH: 204
<212> TYPE: DNA
<213> ORGANISM: Escherichia coli

<400> SEQUENCE: 81
acgatcaata tctattttat cgatcgttta tatcgatcga taagctaata ataaccttttg     60 tcagtaacat gcacagatac gtacagaaag acattcaggg aacaacagaa ccacaattca    120
gaaactccca cagccggacc tccggcactg taacccttta cctgccggta tccacgtttg    180
```
tgggtaccgg cttttttatt cacc                                          204

<210> SEQ ID NO 82
<211> LENGTH: 209
<212> TYPE: DNA
<213> ORGANISM: Escherichia coli

<400> SEQUENCE: 82
tttagcgtat tatcgacacc ggcccttttcc gccgtgttcg gtaataaaat aacctggctt    60
attagtccga attcagacaa atataaataa atcctgctca aaattaaaaa ttctaaccgg   120
taaaagatat tacttaaaca tgtaaattca cttttccttta aaaacaaaa aaccgccaaa   180 atcaggcggt ttttgttgc tggtccggt                                     209

<210> SEQ ID NO 83
<211> LENGTH: 158
<212> TYPE: DNA
<213> ORGANISM: Escherichia coli

<400> SEQUENCE: 83
tgaaatctgt cactgaagaa aattggcaac taaaggttaa aaccgttata acacagtcac    60
cggcgcagag gagacaatgc cggatttaag acgcggatgc actgctgtgt gtactgtaga   120
gtctggcgga tgtcgacaga ctctattttt ttatgcag                           158

<210> SEQ ID NO 84
<211> LENGTH: 93
<212> TYPE: DNA
<213> ORGANISM: Escherichia coli

<400> SEQUENCE: 84
gctatcatca ttaactttat ttattaccgt cattcatttc tgaatgtctg tttaccccta    60
tttcaaccgg atgcctcgca ttcggttttt ttt                                93

<210> SEQ ID NO 85
<211> LENGTH: 110
<212> TYPE: DNA
<213> ORGANISM: Escherichia coli

<400> SEQUENCE: 85
gaaacggagc ggcacctctt ttaaccttg aagtcactgc ccgtttcgag agtttctcaa    60
ctcgaataac taaagccaac gtgaacttt gcggatctcc aggatccgct               110

<210> SEQ ID NO 86
<211> LENGTH: 377
<212> TYPE: DNA
<213> ORGANISM: Escherichia coli

<400> SEQUENCE: 86
gaagctgacc agacagtcgc cgcttcgtcg tcgtcctctt cggggggagac gggcggaggg    60 gaggaaagtc cgggctccat agggcagggt gccaggtaac gcctgggggg gaaacccacg   120
accagtgcaa cagagagcaa accgccgatg gcccgcgcaa gcgggatcag gtaagggtga   180
aagggtgcgg taagagcgca ccgcgcggct ggtaacagtc cgtggcacgg taaactccac   240
ccggagcaag gccaaatagg ggttcataag gtacggcccg tactgaaccc gggtaggctg   300
cttgagccag tgagcgattg ctggcctaga tgaatgactg tccacgacag aacccggctt   360
atcggtcagt ttcacct                                                 377

```
<210> SEQ ID NO 87
<211> LENGTH: 89
<212> TYPE: DNA
<213> ORGANISM: Escherichia coli

<400> SEQUENCE: 87
tcatccctca aggatcgacg ggattagcaa gtcaggaggt cttatgaatg agttcaagag      60
gtgtatgcgc gtgtttagtc attctccct                                       89

<210> SEQ ID NO 88
<211> LENGTH: 68
<212> TYPE: DNA
<213> ORGANISM: Escherichia coli

<400> SEQUENCE: 88
attattctta tcgccccttc aagagctaag ccactgagag tgccggagat aagcgccgga      60
tggggtag                                                              68

<210> SEQ ID NO 89
<211> LENGTH: 249
<212> TYPE: DNA
<213> ORGANISM: Escherichia coli

<400> SEQUENCE: 89
aaagtcagcg aaggaaatgc ttctggcttt taacagataa aaagagaccg aacacgattc      60
ctgtattcgg tccagggaaa tggctcttgg gagagagccg tgcgctaaaa gttggcatta     120
atgcaggctt agttgccttg ccctttaaga atagatgacg acgccaggtt ttccagtttg     180
cgtgcaaaat ggtcaataaa aagcgtggtg gtcatcagct gaaatgttaa aaaccgcccg     240
ttctggtga                                                            249

<210> SEQ ID NO 90
<211> LENGTH: 121
<212> TYPE: DNA
<213> ORGANISM: Escherichia coli

<400> SEQUENCE: 90
gctgatgacc accacgcttt ttattgacca ttttgcacgc aaactggaaa acctggcgtc      60
gtcatctatt cttaaagggc aaggcaacta agcctgcatt aatgccaact tttagcgcac     120
g                                                                    121

<210> SEQ ID NO 91
<211> LENGTH: 149
<212> TYPE: DNA
<213> ORGANISM: Escherichia coli

<400> SEQUENCE: 91
ttgacactaa gggcggagtg acataatttc aggagtgagg gttagggaga ggtttccccc      60 tcccctggt gttcttagta agcctggaag ctaatcacta agagtatcac cagtatgatg     120
acgtgcttca tcataaccct ttccttatt                                      149

<210> SEQ ID NO 92
<211> LENGTH: 143
<212> TYPE: DNA
<213> ORGANISM: Escherichia coli

<400> SEQUENCE: 92
ttgacaatct tatcgtgaag gcatactttc aggagtgagg gtagagcggg gtttccccccg     60 ccctggtagt cttagtaagc ggggaagctt atgactaaga gcaccacgat gatgagtagc    120
```

```
ttcatcatga cccttt cctt att                                           143

<210> SEQ ID NO 93
<211> LENGTH: 304
<212> TYPE: DNA
<213> ORGANISM: Escherichia coli

<400> SEQUENCE: 93 gcggccctttt ccgccgtctc gcaaacgggc gctggcttta ggaaaggatg ttccgtggcc    60
gtaaatgcag gtgtttcaca gcgcttgcta tcgcggcaat atcgccagtg gtgctgtcgt   120
gatgcggtct tcgcatggac cgcacaatga agatacggtg cttttgtatc gtacttattg   180
tttctggtgc gctgttaacc gaggtaaata ataaccggag tctctccggc gacaatttac   240
tggtggttaa caaccttcag agcagcaagt aagcccgaat gccgcccttt gggcggcata   300
tttt                                                                304

<210> SEQ ID NO 94
<211> LENGTH: 151
<212> TYPE: DNA
<213> ORGANISM: Escherichia coli

<400> SEQUENCE: 94
ttgacatcgt tgattctttg acctaattta gtgagtaagg gtaagggagg attgctcctc    60
ccctgagact gactgttaat aagcgctgaa acttatgagt aacagtacaa tcagtatgat   120
gacaagtcgc atcataaccc ttctccttca a                                  151

<210> SEQ ID NO 95
<211> LENGTH: 150
<212> TYPE: DNA
<213> ORGANISM: Escherichia coli

<400> SEQUENCE: 95
ttgacgctga ttttttttca acctaaagta aaggaacaag ggtgagggag gatttctccc    60
ccctctgatt ggctgttaat aagctgcgaa acttacgagt aacaacacaa tcagtatgat   120
gacgagcttc atcataaccc tttccttctg                                    150

<210> SEQ ID NO 96
<211> LENGTH: 227
<212> TYPE: DNA
<213> ORGANISM: Escherichia coli

<400> SEQUENCE: 96
gatgaagcaa gggggtgccc catgcgtcag ttttatcagc actattttac cgcgacagcg    60
aagttgtgct ggttgcgttg gttaagcgtc ccacaacgat taaccatgct tgaaggactg   120
atgcagtggg atgaccgcaa ttctgaaagt tgacttgcct gcatcatgtg tgactgagta   180
ttggtgtaaa atcacccgcc agcagattat acctgctggt tttttttt                227

<210> SEQ ID NO 97
<211> LENGTH: 109
<212> TYPE: DNA
<213> ORGANISM: Escherichia coli

<400> SEQUENCE: 97
gtagggtaca gaggtaagat gttctatctt tcagaccttt tacttcacgt aatcggattt    60
ggctgaatat tttagccgcc ccagtcagta atgactgggg cgttttta               109
```

```
<210> SEQ ID NO 98
<211> LENGTH: 75
<212> TYPE: DNA
<213> ORGANISM: Escherichia coli

<400> SEQUENCE: 98
tgaaagacgc gcatttgtta tcatcatccc tgaattcaga gatgaaattt tggccactca    60
cgagtggcct ttttc                                                     75

<210> SEQ ID NO 99
<211> LENGTH: 174
<212> TYPE: DNA
<213> ORGANISM: Escherichia coli

<400> SEQUENCE: 99
atcttctgcg catcctcgcg actaatgaca accctaaccc agctctatgt gggtaaagcc    60
tctcattagc cgcgcgaacc tctgcaacgg aagatcattc atagcaacaa tacattagtt   120
tccagtgaat tgctgccgtc agcttgaaaa aaggggccac tcaggccccc tttt         174

<210> SEQ ID NO 100
<211> LENGTH: 94
<212> TYPE: DNA
<213> ORGANISM: Escherichia coli

<400> SEQUENCE: 100
gcgatcagga agaccctcgc ggagaacctg aaagcacgac attgctcaca ttgcttccag    60
tattacttag ccagccgggt gctggctttt tttt                                94

<210> SEQ ID NO 101
<211> LENGTH: 172
<212> TYPE: DNA
<213> ORGANISM: Escherichia coli

<400> SEQUENCE: 101
gtagatgctc attccatctc ttatgttcgc cttagtgcct cataaactcc ggaatgacgc    60
agagccgttt acggtgctta tcgtccactg acagatgtcg cttatgcctc atcagacacc   120
atggacacaa cgttgagtga agcacccact tgttgtcata cagacctgtt tt           172

<210> SEQ ID NO 102
<211> LENGTH: 245
<212> TYPE: DNA
<213> ORGANISM: Escherichia coli

<400> SEQUENCE: 102
atagagcgag gacgctaaca ggaacaatga ctcaggatga gggtcaggag cgccaggagg    60
cgaagacaga ggattgtcag gaagacaaac gtccggagac gtaattaaac ggaaatggaa   120
tcaacacgga ttgttccggc taaaggaaaa acagggtgtg ttggcggcct gcaaggattg   180
taagacccgt taagggttat gagtcaggaa aaaaggcgac agagtaatct gtcgcctttt   240
ttctt                                                               245

<210> SEQ ID NO 103
<211> LENGTH: 140
<212> TYPE: DNA
<213> ORGANISM: Escherichia coli

<400> SEQUENCE: 103
atcaacacca accggaacct ccaccacgtg ctcgaatgag gtgtgttgac gtcggggaa     60 accctcctgt gtaccagcgg gatagagaga aagacaaaga ccggaaaaca aactaaagcg   120
```
cccttgtggc gctttagttt 140

<210> SEQ ID NO 104
<211> LENGTH: 93
<212> TYPE: DNA
<213> ORGANISM: Escherichia coli

<400> SEQUENCE: 104
gttctcaacg gggtgccacg cgtacgcgtg cgctgagaaa atacccgtcg aacctgatcc 60
ggataacgcc ggcgaaggga tttgaggctc ctt 93

<210> SEQ ID NO 105
<211> LENGTH: 84
<212> TYPE: DNA
<213> ORGANISM: Escherichia coli

<400> SEQUENCE: 105
acaccgtcgc ttaaagtgac ggcataataa taaaaaaatg aaattcctct ttgacgggcc 60
aatagcgata ttggccattt tttt 84

<210> SEQ ID NO 106
<211> LENGTH: 163
<212> TYPE: DNA
<213> ORGANISM: Escherichia coli

<400> SEQUENCE: 106
actaattaca agaaccaggg gcggaaattc cagccctctc gattgttacg tagcacggac 60
agactatacg cctgatggtc gttccccatc gggcctgaaa accgcaatac gctgggtaac 120
aatcttcgag ggtagcagtt aacgctgcta ccctcttttt tct 163

<210> SEQ ID NO 107
<211> LENGTH: 86
<212> TYPE: DNA
<213> ORGANISM: Escherichia coli

<400> SEQUENCE: 107
ttacgtgacg aagcgcgcgg caaagtggac aataaagcct gagcgttaag tcagtcgtca 60
gacgccggtt aatccggcgt tttttt 86

<210> SEQ ID NO 108
<211> LENGTH: 149
<212> TYPE: DNA
<213> ORGANISM: Escherichia coli

<400> SEQUENCE: 108
agtggctcat tcaccgactt atgtcagccc cttcgggacg tgctacataa aatacgaatg 60
acgcacaaca aggtgcctgc cgtccaactt ctgatatcag cgtagctata tcaaccatcg 120
ggcgaaacgt cgagttaggc accgcctta 149

<210> SEQ ID NO 109
<211> LENGTH: 149
<212> TYPE: DNA
<213> ORGANISM: Escherichia coli

<400> SEQUENCE: 109
gcttattctc agggcggggc gaaattcccc accggcggta aatcaactca gttgaaagcc 60
cgcgagcgct ttgggtgcga actcaaagga cagcagatcc ggtgtaattc cggggccgac 120
ggttagagtc cggatgggag agagtaacg 149

<210> SEQ ID NO 110
<211> LENGTH: 161
<212> TYPE: DNA
<213> ORGANISM: Escherichia coli

<400> SEQUENCE: 110

```
gaaaataaga acacatgttc tcatcttcca ggatgcagca gactgaagaa attcagacat        60
cccgcaacct gcgattatcg caaggtcaag gcaaagtccg gtaatggcgt tctgaatacc       120
agagataatt ctctggcgaa acccaccttaa aggtgggttt t                          161
```

<210> SEQ ID NO 111
<211> LENGTH: 363
<212> TYPE: DNA
<213> ORGANISM: Escherichia coli

<400> SEQUENCE: 111

```
ggggctgatt ctggattcga cgggatttgc gaaacccaag gtgcatgccg aggggcggtt        60
ggcctcgtaa aaagccgcaa aaatagtcg caaacgacga aaactacgct ttagcagctt       120
aataacctgc ttagagccct ctctccctag cctccgctct taggacgggg atcaagagag      180
gtcaaaccca aagagatcg cgtggaagcc ctgcctgggg ttgaagcgtt aaaacttaat       240
caggctagtt tgttagtggc gtgtccgtcc gcagctggca agcgaatgta aagactgact      300
aagcatgtag taccgaggat gtaggaattt cggacgcggg ttcaactccc gccagctcca     360
cca                                                                   363
```

<210> SEQ ID NO 112
<211> LENGTH: 183
<212> TYPE: DNA
<213> ORGANISM: Escherichia coli

<400> SEQUENCE: 112

```
atttctctga gatgttcgca agcgggccag tcccctgagc cgatatttca taccacaaga        60
atgtggcgct ccgcggttgg tgagcatgct cggtccgtcc gagaagcctt aaaactgcga      120
cgacacattc accttgaacc aagggttcaa gggttacagc ctgcggcggc atctcggaga      180
ttc                                                                   183
```

<210> SEQ ID NO 113
<211> LENGTH: 136
<212> TYPE: DNA
<213> ORGANISM: Escherichia coli

<400> SEQUENCE: 113

```
cggacttccg atccatttcg tatacacaga ctggacggaa gcgacaatct cactttgtgt        60
aacaacacac acgtatcggc acatattccg gggtgccctt tggggtcggt aatatgggat      120
acgtggaggc ataacc                                                     136
```

<210> SEQ ID NO 114
<211> LENGTH: 161
<212> TYPE: DNA
<213> ORGANISM: Escherichia coli

<400> SEQUENCE: 114

```
actaattctt tcgttgctcc agacgacgca gagaacgctc acggcggctc tcttcacgac        60
ttctgtcgag caaatttct tcgataaagg ccagatggcg atgcgatgct tcgcgcgctt       120
cttccggctt accggccata atcgcttcaa atatgcgggt g                          161
```

<210> SEQ ID NO 115
<211> LENGTH: 89
<212> TYPE: DNA
<213> ORGANISM: Escherichia coli

<400> SEQUENCE: 115
tcgccctata acgggtaat tatactgaca cgggcgaagg ggaatttcct ctccgcccgt      60
gcattcatct agggggcaatt taaaaaaga                                      89

<210> SEQ ID NO 116
<211> LENGTH: 436
<212> TYPE: DNA
<213> ORGANISM: Escherichia coli

<400> SEQUENCE: 116
aaagccataa aaaccatgag gttattatgg ccgatttgag gagggaaaga gtaagagcag      60
tttgttaaat gtacaacgac gattctccca ccgggcgcgt tttaaagcga cggtggatcc     120
agaggtactg ctccggtgcg cgcatgatct ctttctcgat aatcttgttc ataggcag       180 cggcttgatt ttcatctgtc gggtagcctt ccatctctgg ggtgatgaac aaacgatatc    240
cgctgtaatc cgcttttctt accatcgtta cggtcaacat ggctgcgcca gagagacggg    300
agagaacata ggtgccattg gttgtggcga cattttccac cgcaaagaac ggcgcgaagg    360
agctgccttt acgaccataa tcctgatcgg gagcaaacca taccgcttca cctttcttca    420
gtgcaccgac aatgcc                                                   436

<210> SEQ ID NO 117
<211> LENGTH: 58
<212> TYPE: DNA
<213> ORGANISM: Artificial sequence
<220> FEATURE:
<223> OTHER INFORMATION: primer

<400> SEQUENCE: 117
gcgaaaaaaa acctgcgcat ccgcgcaggt tggtgcaaga tgaagcctgc tttttttat       58

<210> SEQ ID NO 118
<211> LENGTH: 58
<212> TYPE: DNA
<213> ORGANISM: Artificial sequence
<220> FEATURE:
<223> OTHER INFORMATION: primer

<400> SEQUENCE: 118
tggcgtttgg cttcaggttg ctaaagtggt gatcccagag cgctcaagtt agtataaa        58

<210> SEQ ID NO 119
<211> LENGTH: 58
<212> TYPE: DNA
<213> ORGANISM: Artificial sequence
<220> FEATURE:
<223> OTHER INFORMATION: primer

<400> SEQUENCE: 119
acttcctgag ccggaacgaa aagttttatc ggaatgcgtg tgaagcctgc tttttttat       58

<210> SEQ ID NO 120
<211> LENGTH: 58
<212> TYPE: DNA
<213> ORGANISM: Artificial sequence
<220> FEATURE:
<223> OTHER INFORMATION: primer

```
<400> SEQUENCE: 120
aagcaccgca attaggcggt gctacattaa tcactatgga cgctcaagtt agtataaa         58
```